(12) United States Patent
Robaina et al.

(10) Patent No.: US 11,559,228 B2
(45) Date of Patent: Jan. 24, 2023

(54) AUGMENTED AND VIRTUAL REALITY EYEWEAR, SYSTEMS, AND METHODS FOR DELIVERING POLARIZED LIGHT AND DETERMINING GLUCOSE LEVELS

(71) Applicant: Magic Leap, Inc., Plantation, FL (US)

(72) Inventors: Nastasja U. Robaina, Coconut Grove, FL (US); Nicole Elizabeth Samec, Fort Lauderdale, FL (US); Mark Baerenrodt, Delray Beach, FL (US)

(73) Assignee: Magic Leap, Inc., Plantation, FL (US)

( * ) Notice: Subject to any disclaimer, the term of this patent is extended or adjusted under 35 U.S.C. 154(b) by 455 days.

(21) Appl. No.: 15/807,486

(22) Filed: Nov. 8, 2017

(65) Prior Publication Data

US 2018/0160956 A1 Jun. 14, 2018

Related U.S. Application Data

(60) Provisional application No. 62/433,756, filed on Dec. 13, 2016.

(51) Int. Cl.
*A61B 5/1455* (2006.01)
*A61B 5/145* (2006.01)
(Continued)

(52) U.S. Cl.
CPC ........ *A61B 5/14558* (2013.01); *A61B 5/0205* (2013.01); *A61B 5/02055* (2013.01);
(Continued)

(58) Field of Classification Search
CPC . A61B 5/14558; A61B 5/14532; A61B 5/145; A61B 5/1455; A61B 5/486; A61B 5/6803; G06T 19/006
See application file for complete search history.

(56) References Cited

U.S. PATENT DOCUMENTS 4,014,321 A 3/1977 March
5,209,231 A 5/1993 Cote et al.
(Continued)

FOREIGN PATENT DOCUMENTS

CN 1650148 A 8/2005
CN 101854845 A 10/2010
(Continued)

OTHER PUBLICATIONS

International Search Report and Written Opinion for PCT Application No. PCT/US2017/60695, dated Jan. 22, 2018 in 12 pages.
(Continued)

*Primary Examiner* — Devin B Henson
(74) *Attorney, Agent, or Firm* — Knobbe, Martens, Olson & Bear, LLP

(57) ABSTRACT

Various embodiments of a user-wearable device can comprise a frame configured to mount on a user. The device can include a display attached to the frame and configured to direct virtual images to an eye of the user. The device can also include a light source configured to provide polarized light to the eye of the user and that the polarized light is configured to reflect from the eye of the user. The device can further include a light analyzer configured to determine a polarization angle rotation of the reflected light from the eye of the user such that a glucose level of the user can be determined based at least in part on the polarization angle rotation of the reflected light.

24 Claims, 18 Drawing Sheets

(51) Int. Cl.
*A61B 5/00* (2006.01)
*G06T 19/00* (2011.01)
*A61B 5/0205* (2006.01)
*A61B 5/08* (2006.01)
*A61B 5/024* (2006.01)

(52) U.S. Cl.
CPC ............ *A61B 5/145* (2013.01); *A61B 5/1455* (2013.01); *A61B 5/14532* (2013.01); *A61B 5/4266* (2013.01); *A61B 5/486* (2013.01); *A61B 5/6803* (2013.01); *G06T 19/006* (2013.01); *A61B 5/024* (2013.01); *A61B 5/0816* (2013.01)

(56) References Cited

U.S. PATENT DOCUMENTS

| | | | |
|---|---|---|---|
| 5,687,721 | A | 11/1997 | Kuhls |
| 5,788,632 | A | 8/1998 | Pezzaniti et al. |
| 6,370,407 | B1 | 4/2002 | Kroeger et al. |
| 6,493,474 | B1 | 12/2002 | Yao |
| 6,704,588 | B2* | 3/2004 | Ansari ............... A61B 5/14532 600/319 |
| 6,850,221 | B1 | 2/2005 | Tickle |
| 6,885,782 | B2 | 4/2005 | Wood et al. |
| 9,081,426 | B2 | 7/2015 | Armstrong |
| 2001/0031914 | A1 | 10/2001 | Gobeli |
| 2003/0223037 | A1 | 12/2003 | Chernyak |
| 2003/0225321 | A1 | 12/2003 | Cote et al. |
| 2003/0233036 | A1 | 12/2003 | Ansari et al. |
| 2006/0028436 | A1 | 2/2006 | Armstrong |
| 2006/0074290 | A1 | 4/2006 | Chen et al. |
| 2006/0258920 | A1 | 11/2006 | Burd |
| 2007/0081123 | A1 | 4/2007 | Lewis |
| 2009/0093798 | A1 | 4/2009 | Charles |
| 2011/0124996 | A1* | 5/2011 | Reinke ............... A61M 5/14248 600/365 |
| 2011/0184262 | A1* | 7/2011 | Menon ............... A61B 5/14546 600/318 |
| 2012/0127062 | A1 | 5/2012 | Bar-Zeev et al. |
| 2012/0162549 | A1 | 6/2012 | Gao et al. |
| 2012/0245447 | A1* | 9/2012 | Karan ............... A61B 5/14532 600/365 |
| 2012/0277557 | A1 | 11/2012 | Li et al. |
| 2013/0082922 | A1 | 4/2013 | Miller |
| 2013/0117377 | A1 | 5/2013 | Miller |
| 2013/0125027 | A1 | 5/2013 | Abovitz |
| 2013/0208234 | A1 | 8/2013 | Lewis |
| 2013/0242262 | A1 | 9/2013 | Lewis |
| 2014/0039383 | A1 | 2/2014 | Dobbies et al. |
| 2014/0071539 | A1 | 3/2014 | Gao |
| 2014/0152988 | A1 | 6/2014 | Liu et al. |
| 2014/0177023 | A1 | 6/2014 | Gao et al. |
| 2014/0218468 | A1 | 8/2014 | Gao et al. |
| 2014/0267420 | A1 | 9/2014 | Schowengerdt |
| 2014/0306866 | A1 | 10/2014 | Miller et al. |
| 2014/0379273 | A1 | 12/2014 | Petisce et al. |
| 2015/0016777 | A1 | 1/2015 | Abovitz et al. |
| 2015/0103306 | A1 | 4/2015 | Kaji et al. |
| 2015/0178939 | A1 | 6/2015 | Bradski et al. |
| 2015/0205126 | A1 | 7/2015 | Schowengerdt |
| 2015/0222883 | A1 | 8/2015 | Welch |
| 2015/0222884 | A1 | 8/2015 | Cheng |
| 2015/0268415 | A1 | 9/2015 | Schowengerdt et al. |
| 2015/0302652 | A1 | 10/2015 | Miller et al. |
| 2015/0309263 | A2 | 10/2015 | Abovitz et al. |
| 2015/0326570 | A1 | 11/2015 | Publicover et al. |
| 2015/0346490 | A1 | 12/2015 | TeKolste et al. |
| 2015/0346495 | A1 | 12/2015 | Welch et al. |
| 2016/0011419 | A1 | 1/2016 | Gao |
| 2016/0026253 | A1 | 1/2016 | Bradski et al. |
| 2016/0077547 | A1 | 3/2016 | Aimone et al. |
| 2016/0235374 | A1 | 8/2016 | Miller et al. |
| 2016/0256086 | A1* | 9/2016 | Byrd .................... A61B 5/0059 |
| 2016/0270656 | A1 | 9/2016 | Samec et al. |
| 2016/0298956 | A1 | 10/2016 | Li et al. |
| 2018/0014723 | A1 | 1/2018 | Hane et al. |

FOREIGN PATENT DOCUMENTS

| | | |
|---|---|---|
| CN | 103845063 A | 6/2014 |
| JP | 2010-197474 | 9/2010 |
| JP | 2015-506733 A | 3/2015 |
| JP | 2015-192861 A | 11/2015 |
| JP | 2016-189858 A | 11/2016 |
| JP | 2016-200596 A | 12/2016 |
| WO | WO 2018/111449 | 6/2018 |

OTHER PUBLICATIONS

International Preliminary Report on Patentability for PCT Application No. PCT/US2017/60695, dated Jun. 18, 2019. in 6 pages.
Blamire, Prof. John "Exporing Life @ BIOdotEDU," 2004. http://www.brooklyn.cuny.edu/bc/ahp/LAD/C4c/C4c_polarizer.html in 4 pages.
Collett E., "The General Photonics Polarite II™ Polarization Controller" in Polarized Light in Fiber Optics. SPIE Press (2003) Chapter 9.11, pp. 219-226.
Hardesty, Larry "Making 3-D imaging 1,000 times better— Algorithms exploiting light's polarization boost resolution of commercial depth sensors 1,000-fold," MIT News Office, Dec. 1, 2015. http://news.mit.edu/2015/algorithms-boost-3-d-imaging-resoiution-1000-times-1201 in 3 pages.
"Light Box Kits," Optical activity of glucose, as archived Apr. 20, 2016. https://web.archive.org/web/20150420034103/http://www.lightboxkit.com/Assay_GlucoseByPolarizedLight.html in 3 pages.
Newport Research Corporation, "Tutorial: Polarization in Fiber Optics"; as archived May 2, 2016. <https://www.newport.com:80/Tutoriai-Polarization-in-Fiber-Optics/849671/1033/content.aspx> in 3 pages.
Pelletier C.C. et al., "Determination of Glucose in Human Aqueous Humor Using Raman Spectroscopy and Designed-Solution Calibration", Applied Spectroscopy (2005) 59(8):1024-1031.
"Optical Activity," University of Nebraska, Department of Physics and Astronomy, Polarized Electron Physics, as archived Sep. 24, 2015. https://web.archive.org/web/20150924042052/http://physics.unl.edu/~tgay/contentOA2.html in 3 pages.
Poddar R. et al., "Non-Invasive Glucose Monitoring Techniques: A Review and current trends", Cornell University Library; arXIV preprint arXiv:0810.5755v1 [physics.med-ph] Oct. 31, 2008 in 47 pages.
"Polarization," The Physics Classroom, as archived Oct. 5, 2016. https://web.archive.org/web/20161005200104/https://www.physicsclassroom.com/class/light/Lesson-1/Polarization in 8 pages.
Ansari, et al., "New optical scheme for a polarimetric-based glucose sensor," Journal of Biomedical Optics 9(1), 103-115, Jan./Feb. 2004.
ARToolKit: https://web.archive.org/web/20051013062315/http://www.hitl.washington.edu:80/artoolkit/documentation/hardware.htm, archived Oct. 13, 2005.
Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.
Azuma, "Predictive Tracking for Augmented Realty," TR95-007, Department of Computer Science, UNC-Chapei Hill, NC, Feb. 1995.
Bimber, et al., "Spatial Augmented Reality—Merging Real and Virtual Worlds," 2005 https://web.media.mit.edu/~raskar/book/BimberRaskarAugmentedReaiityBook.pdf.
Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288. Oxford University Press, New York (1995).
Tanriverdi and Jacob, "Interacting With Eye Movements in Virtual Environments," Department of Electrical Engineering and Com-

(56) References Cited

OTHER PUBLICATIONS puter Science, Tufts University, Medford, MA—paper/Proc. ACM CHI 2000 Human Factors in Computing Systems Conference, pp. 265-272, Addison-Wesley/ACM Press (2000).
Suisheng, Optoelectronics Technology: A New World of Information Weaponry, p. 352. Published Jan. 1, 2008, ISBN: 9787118051476.
Chinese Rejection of Decision, re CN Application No. 201780086316.9, dated Jan. 29, 2022.
Yao, "Polarization in Fiber Systems: Squeezing out More Bandwidth," General Photonics Corp., Reprinted from the 2003 issue of The Photonics Handbook® Laurin Publishing, 5 pages.

\* cited by examiner

AUGMENTED AND VIRTUAL REALITY EYEWEAR, SYSTEMS, AND METHODS FOR DELIVERING POLARIZED LIGHT AND DETERMINING GLUCOSE LEVELS

PRIORITY CLAIM

This application claims the benefit of priority under 35 U.S.C. 119(e) of U.S. Provisional Application No. 62/433,756 filed on Dec. 13, 2016, the entire disclosure of which is expressly incorporated herein by reference.

INCORPORATION BY REFERENCE

This application incorporates by reference the entirety of each of the following patent applications: U.S. application Ser. No. 14/555,585 filed on Nov. 27, 2014; U.S. application Ser. No. 14/690,401 filed on Apr. 18, 2015; U.S. application Ser. No. 14/212,961 filed on Mar. 14, 2014; U.S. application Ser. No. 14/331,218 filed on Jul. 14, 2014; and U.S. application Ser. No. 15/072,290 filed on Mar. 16, 2016.

BACKGROUND

Field

The present disclosure relates to optical devices, including virtual reality and augmented reality imaging and visualization eyewear, systems, and methods for delivering polarized light and determining glucose levels.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, in an MR scenario, AR image content may be blocked by or otherwise be perceived as interacting with objects in the real world.

Referring to FIG. 1A, an augmented reality scene 1 is depicted wherein a user of an AR technology sees a real-world park-like setting 1100 featuring people, trees, buildings in the background, and a concrete platform 1120. In addition to these items, the user of the AR technology also perceives that he "sees" "virtual content" such as a robot statue 1110 standing upon the real-world platform 1120, and a cartoon-like avatar character 1130 flying by which seems to be a personification of a bumble bee, even though these elements 1110, 1130 do not exist in the real world. Because the human visual perception system is complex, it is challenging to produce an AR technology that facilitates a comfortable, natural-feeling, rich presentation of virtual image elements amongst other virtual or real-world imagery elements.

Devices, systems, and methods disclosed herein address various challenges related to AR and VR technology.

SUMMARY

The devices, systems, and methods of the disclosure each have several innovative aspects, no single one of which is solely responsible for the desirable attributes disclosed herein.

1. A user-wearable device comprising:
   a frame configured to mount on a user;
   a display attached to the frame, the display configured to direct virtual images to an eye of the user;
   a light source configured to provide polarized light to the eye of the user, wherein the polarized light is configured to reflect from the eye of the user; and
   a light analyzer configured to determine a polarization angle rotation of the reflected light from the eye of the user such that a glucose level of the user can be determined based at least in part on the polarization angle rotation of the reflected light.

2. The user-wearable device of Example 1, wherein the light source comprises a polarizing filter.

3. The user-wearable device of Example 1 or 2, wherein the light source comprises a polarization controller.

4. The user-wearable device of Example 3, wherein the polarization controller comprises at least one optical fiber.

5. The user-wearable device of Example 4, wherein the polarization controller further comprises at least one actuator configured to apply pressure on the at least one optical fiber.

6. The user-wearable device of Example 5, wherein the at least one actuator comprises at least one piezo-electric actuator.

7. The user-wearable device of any of the previous Examples, wherein the light source comprises a source of light having a wavelength in the range of 500 nm to 800 nm.

8. The user-wearable device of Example 7, wherein the light source comprises a laser configured to emit light having a wavelength in the range of 530 nm to 650 nm.

9. The user-wearable device of Example 8, wherein the light source comprises a laser configured to emit light having a wavelength in the range of 550 nm to 590 nm.

10. The user-wearable device of any of the previous Examples,
    wherein the light analyzer comprises a rotatable filter configured to block at least a portion of the reflected light, and
    wherein the light analyzer is configured to determine the polarization angle rotation of the reflected light based at least in part on the blocked reflected light.

11. The user-wearable device of any of the previous Examples, further comprising processing electronics configured to determine the glucose level of the user based at least in part on the polarization angle rotation of the reflected light.

12. The user-wearable device of Example 11, wherein the processing electronics is configured to determine a concentration of the glucose level based at least in part on the determined polarization angle rotation of the reflected light.

13. The user-wearable device of any of the previous Examples, wherein the device is configured to communicate with the user or with a clinician.

14. The user-wearable device of Example 13, wherein the device is configured to communicate the determined glucose level to the user or clinician.

15. The user-wearable device of Example 13 or 14, wherein the device is configured to receive information from the user or clinician.

16. The user-wearable device of Example 15, wherein the processing electronics is configured to calibrate the determined glucose level based at least in part on the received information from the user or clinician.

17. The user-wearable device of Example 16, wherein the received information includes a glucose level determined by blood testing.

18. The user-wearable device of any of Examples 13-17, wherein the processing electronics is configured to determine the glucose level upon request from the user or clinician.

19. The user-wearable device of any of Examples 11-18, wherein the processing electronics is configured to determine the glucose level automatically for at least a period of time.

20. The user-wearable device of any of Examples 13-19, wherein the device is configured to communicate with the user via the augmented reality display.

21. The user-wearable device of any of Examples 13-20, wherein the device is configured to communicate with the user via a display separate from the augmented reality display.

22. The user-wearable device of any of Examples 11-21, wherein the processing electronics is configured to remotely store and access the determined glucose level.

23. The user-wearable device of any of Examples 11-22, wherein the processing electronics is configured to remotely store and access information relating to the determined glucose level.

24. The user-wearable device of Example 22 or 23, wherein the device is configured to track the glucose level of the user over time.

25. The user-wearable device of Example 24, wherein the device is configured to compare a contemporaneous glucose level with a historical glucose level.

26. The user-wearable device of Example 25, wherein the device is configured to provide an alert to the user or clinician in response to comparing the contemporaneous glucose level with the historical glucose level.

27. The user-wearable device of any of the preceding Examples, further comprising one or more sensors configured to detect at least one parameter relating to a physical state of the user.

28. The user-wearable device of Example 27, wherein the one or more sensors comprises an inwardly or outwardly facing camera.

29. The user-wearable device of Example 27 or 28, wherein the at least one parameter comprises body temperature, skin temperature, heart rate, respiration rate, level of sweating, time elapsed since last meal, or time elapsed since last medication.

30. The user-wearable device of any of Examples 27-29, wherein the device is configured to analyze the determined glucose level based at least in part on the at least one parameter relating to the physical state of the user.

31. The user-wearable device of any of Examples 27-30, wherein the device is configured to provide an alert to the user or clinician when the at least one parameter falls outside a range.

32. The user-wearable device of any of the preceding Examples, further comprising an eye tracking sensor configured to determine if the provided polarized light transmits into the eye of the user.

33. The user-wearable device of Example 32, wherein the device is configured to not determine the glucose level when the eye tracking sensor determines the polarized light did not transmit into the eye of the user.

34. The user-wearable device of any of the preceding Examples, wherein at least a portion of the light source or the light analyzer is configured to rotate such that the polarization angle rotation can be determined.

35. The user-wearable device of any of the previous Examples, further comprising an optical detector disposed with respect to the analyzer to detect the amount of polarized light reflected from the eye that passes through the analyzer.

36. The user-wearable device of any of the preceding Examples, further comprising an eye tracking sensor configured to determine if the provided polarized light is incident on the iris or retinal vasculature of the user.

37. The user-wearable device of any of the preceding Examples, further comprising an eye tracking sensor configured to determine if the provided polarized light is incident on the same location of the eye.

38. The user-wearable device of any of the preceding Examples, further comprising one or more sensors configured to detect an activity or condition of the user.

39. The user-wearable device of Example 38, wherein the activity comprises eating, taking medication, exercising, or a combination thereof.

40. The user-wearable device of Example 38 or 39, wherein the device is configured to provide real time feedback relating to the activity or condition to the user.

41. The user-wearable device of Example 19, wherein the processing electronics is configured to:
determine whether to re-determine the glucose level; and
if determined, automatically re-determine the glucose level.

42. The user-wearable device of any of the preceding Examples above, wherein the display is configured to direct different virtual images to an eye of the user with different amounts of divergence or collimation.

43. The user-wearable device of any of the Examples above, wherein the display is configured to transmit light from a surrounding environment to the user's eyes to allow a view of that surrounding environment.

Additional Examples

1. A user-wearable device comprising:
a frame configured to mount on a user;
a display attached to the frame, the display configured to direct virtual images to an eye of the user;
a light source configured to provide light to the eye of the user;
a light analyzer configured to analyze the light reflected from the eye of the user; and
processing electronics in communication with the light analyzer, the processing electronics configured to determine a glucose level of the user based at least in part on light reflected from the eye of the user, the processing electronics configured to determine the glucose level of the user automatically for at least a period of time.

2. The user-wearable device of Example 1, wherein the processing electronics is configured to determine the glucose level of the user automatically as programmed by the user or a clinician.

3. The user-wearable device of Example 1 or 2, wherein the processing electronics is configured to determine the glucose level of the user multiple times a day.

4. The user-wearable device of Example 3, wherein the processing electronics is configured to determine the glucose level of the user at least 3 times a day.

5. The user-wearable device of Example 1 or 2, wherein the processing electronics is configured to determine the glucose level of the user multiple times a week.

6. The user-wearable device of Example 5, wherein the processing electronics is configured to determine the glucose level of the user at least 3 times a week.

7. The user-wearable device of any of the previous Examples, wherein the device is configured to communicate with the user or with a clinician.

8. The user-wearable device of Example 7, wherein the device is configured to communicate the determined glucose level to the user or clinician.

9. The user-wearable device of any of Examples 7-8, wherein the device is configured to communicate with the user via the display.

10. The user-wearable device of any of Examples 7-8, wherein the device is configured to communicate with the user via a display separate from the display.

11. The user-wearable device of any of the previous Examples, wherein the device is configured to provide an alert to the user or clinician in response to the determined glucose level.

12. The user-wearable device of any of Examples 1-11, wherein the processing electronics is configured to store and access the determined glucose level.

13. The user-wearable device of any of Examples 1-11, wherein the processing electronics is configured to remotely store and access the determined glucose level.

14. The user-wearable device of Example 12 or 13, wherein the device is configured to track the glucose level of the user over time.

15. The user-wearable device of Example 14, wherein the device is configured to compare a contemporaneous glucose level with a historical glucose level.

16. The user-wearable device of Example 15, wherein the device is configured to provide an alert to the user or clinician in response to comparing the contemporaneous glucose level with the historical glucose level.

17. The user-wearable device of any of the previous Examples, wherein the processing electronics is configured to:
determine whether to re-determine the glucose level; and
if determined, automatically re-determine the glucose level.

18. The user-wearable device of any of the previous Examples, wherein the light source is configured to provide polarized light, and the processing electronics is configured to determine the glucose level based at least in part on a polarization angle rotation of the polarized light.

19. The user-wearable device of any of the Examples above, wherein the display is configured to direct different virtual images to an eye of the user with different amounts of divergence or collimation.

20. The user-wearable device of any of the Examples above, wherein the display is configured to transmit light from a surrounding environment to the user's eyes to allow a view of that surrounding environment.

Further Examples

1. A user-wearable device comprising:
a frame configured to mount on a user;
a display attached to the frame, the display configured to direct virtual images to an eye of the user;
a light source configured to provide light to the eye of the user;
a light analyzer configured to analyze the light reflected from the eye of the user;
one or more sensors attached to the frame, the one or more sensors configured to sense information relating to the user or environment; and
processing electronics in communication with the light analyzer and the one or more sensors, the processing electronics configured to:
determine a glucose level of the user based at least in part on the light reflected from the eye of the user;
receive from the one or more sensors the information relating to the user or the environment; and
store and access the received information.

2. The user-wearable device of Example 1, wherein the one or more sensors comprise one or more user sensors.

3. The user-wearable device of any of Examples 1-2, wherein the one or more sensors comprise one or more environmental sensors.

4. The user-wearable device of any of Examples 1-3, wherein the one or more sensors comprise one or more user sensors and one or more environmental sensors.

5. The user-wearable device of any of Examples 1-4, wherein the one or more sensors comprise an inwardly or outwardly facing camera.

6. The user-wearable device of any of Examples 1-5, wherein the information relating to the user or the environment comprises an activity of the user, 7. The user-wearable device of Example 6, wherein the activity of the user comprises eating, taking medication, exercising, or a combination thereof.

8. The user-wearable device of any of Examples 1-7, wherein the information relating to the user or the environment comprises food intake, nutritional information of food, medication intake, or combinations thereof.

9. The user-wearable device of any of Examples 1-8, wherein the information relating to the user or the environment comprises at least one of parameter relating to a physical state of the user.

10. The user-wearable device of Example 9, wherein the at least one parameter comprises body temperature, skin temperature, heart rate, respiration rate, level of sweating, time elapsed since last meal, or time elapsed since last medication.

11. The user-wearable device of any of Examples 1-10, wherein the processing electronics is configured to remotely store and access the information relating to the user or the environment.

12. The user-wearable device of any of Examples 1-11, wherein the device is configured to track the information relating to the user or the environment over time.

13. The user-wearable device of any of Examples 1-12, wherein the processing electronics is configured to store and access the determined glucose level.

14. The user-wearable device of Example 13, wherein the processing electronics is configured to remotely store and access the determined glucose level.

15. The user-wearable device of Example 13 or 14, wherein the device is configured to track the glucose level of the user over time.

16. The user-wearable device of Example 15, wherein the device is configured to compare a contemporaneous glucose level with a historical glucose level.

17. The user-wearable device of any of Examples 1-16, wherein the device is configured to determine relationships between the determined glucose level and at least one aspect of the user or the user's environment.

18. The user-wearable device of any of Examples 1-17, wherein the device is configured to correlate changes in a user's glucose level with one or more of the information relating to the user or the environment.

19. The user-wearable device of any of the previous Examples, wherein the device is configured to communicate with the user or a clinician.

20. The user-wearable device of Example 19, wherein the device is configured to communicate the determined glucose level to the user or clinician.

21. The user-wearable device of Example 19, wherein the device is configured to provide an alert to the user or clinician in response to the determined glucose level or the information relating to the user or the environment.

22. The user-wearable device of any of Examples 9-21, wherein the device is configured to provide an alert to the user or clinician when the at least one parameter falls outside a range.

23. The user-wearable device of any of the previous Examples, wherein the processing electronics is configured to:
  determine whether to re-determine the glucose level; and
  if determined, automatically re-determine the glucose level.

24. The user-wearable device of any of the previous Examples, wherein the light source is configured to provide polarized light, and the processing electronics is configured to determine the glucose level based at least in part on a polarization angle rotation of the polarized light.

25. The user-wearable device of any of the Examples above, wherein the display is configured to direct different virtual images to an eye of the user with different amounts of divergence or collimation.

26. The user-wearable device of any of the Examples above, wherein the display is configured to transmit light from a surrounding environment to the user's eyes to allow a view of that surrounding environment.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Figure 1A:
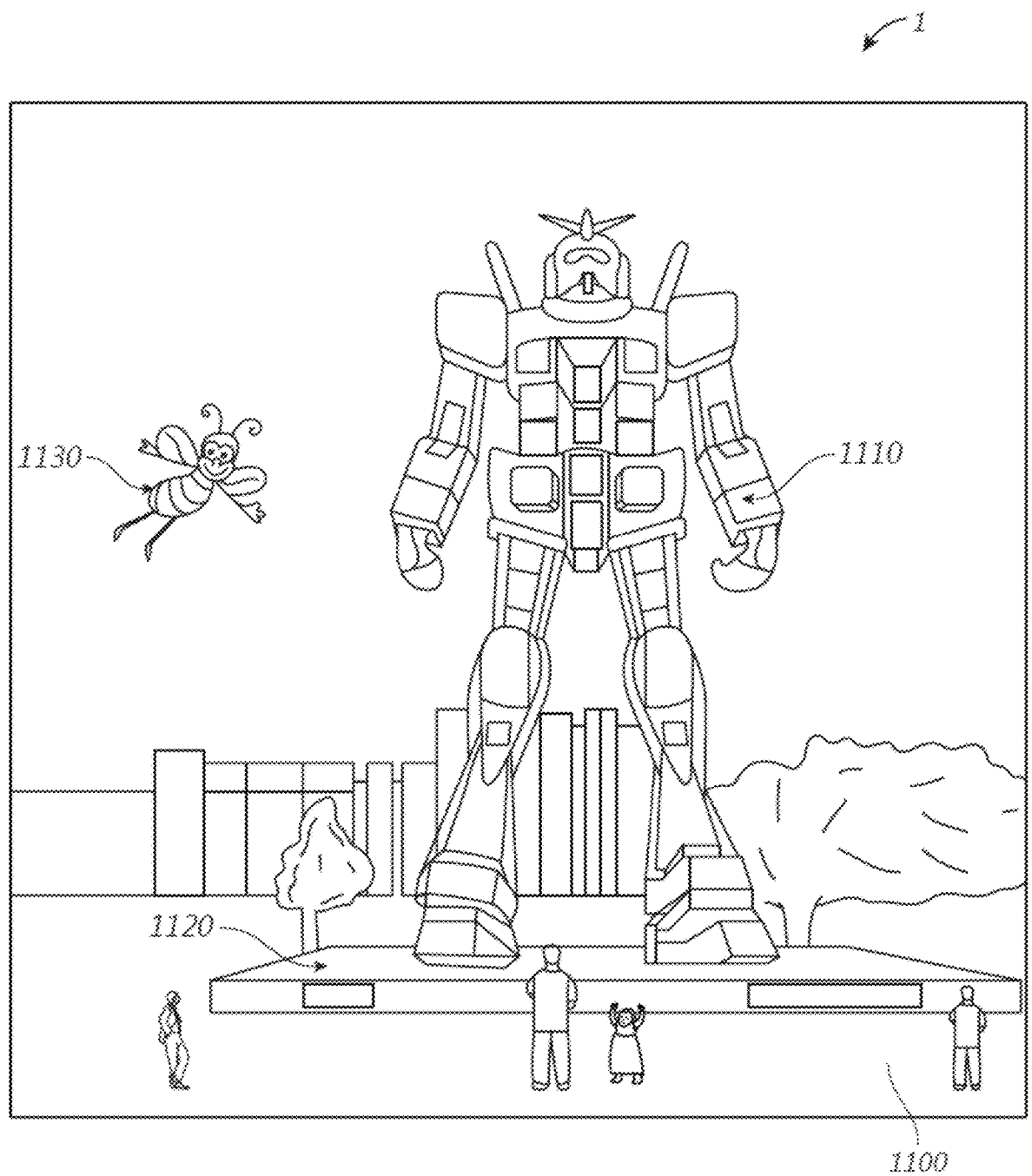
FIG. 1A illustrates a user's view of augmented reality (AR) through an AR device.

Diabetic and other patients may have to monitor their glucose level. Current methods to measure glucose levels include blood testing which involve an invasive skin puncture technique to draw blood. Some patients may have to carry and maintain their own blood glucose test kits (blood glucose meter, lancing device/lancets, test strips, etc.), set alarms to remember to take measurements at certain times of the day, record glucose measurements in a log, and keep food intake/exercise logs. Some patients may also need to visit their doctor multiple times a week to review the logs and adjust their diet and/or lifestyle according to their doctor's recommendation. Such methods can be disruptive to one's day, burdensome, time-consuming, and painful. Various embodiments described herein are directed to user-wearable devices, systems, and methods configured to advantageously allow the determination of glucose level in a non-invasive, pain-free method without the drawing of blood (e.g., determining glucose level based on light reflected from the eye). Users of such embodiments can check their glucose levels more frequently, even multiple times a day. Some embodiments described herein are also configured to conveniently track the determined glucose levels, the user's physical state (e.g., user's temperature), the user's activities (e.g., food intake, exercise, etc.) and/or environmental conditions (e.g., weather). In some such embodiments, the glucose measurements and data tracking can be performed with less user involvement (e.g., partially and/or fully automated in some instances) and also can be remotely shared with a doctor.

Figure 1B:
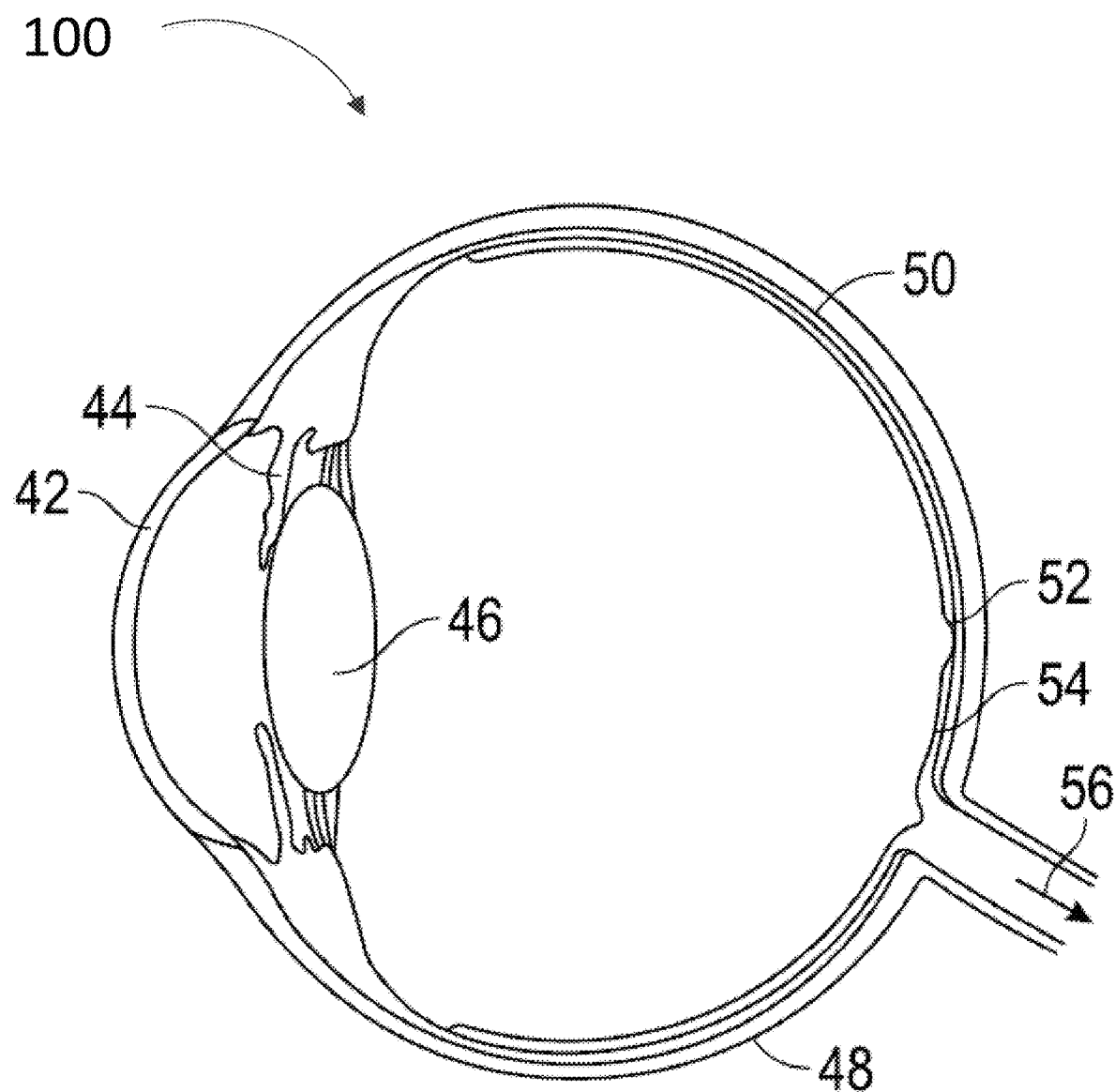
FIG. 1B illustrates a cross-section of a human eye.

As shown in FIG. 1B, a schematic cross-sectional view of a human eye 100 is depicted featuring a cornea 42, iris 44, lens—or "crystalline lens" 46, sclera 48, choroid layer 50, macula 52, retina 54, and optic nerve pathway 56 to the brain. The cornea 42 and the crystalline lens 46 refract and focus the light toward the retina 54. The aqueous humor is a thin, watery fluid located between the cornea 42 and the iris 44 (e.g., in the anterior chamber) and between the iris 44 and the lens 46 (e.g., in the posterior chamber).

Glucose exists in the aqueous humor in both the anterior and posterior chambers of the eye. Glucose molecules are chiral molecules which can cause the polarization angle of linearly polarized light (e.g., the plane of polarization) to rotate. Without being limited by theory, the amount of the polarization angle rotation can be related to the glucose concentration. Various embodiments described herein allow for the determination of glucose levels by projecting polarized light into a user's eye (e.g., in the aqueous humor) and measuring the polarization angle rotation of light reflected from the eye (e.g., caused by glucose molecules in the aqueous humor as the light transmits through the molecules).

Certain embodiments of user-wearable devices and systems described herein may include augmented reality (AR) devices and systems that display virtual content to a user, or viewer, while still allowing the user to see the world around them. Preferably, this content is displayed on a head-mounted display, e.g., as part of eyewear, that projects image information to the user's eyes. In addition, the display may also transmit light from the surrounding environment to the user's eyes, to allow a view of that surrounding environment. As used herein, it will be appreciated that a "head-mounted" display is a display that may be mounted on the head of a viewer.

As discussed further below, many VR, AR, and MR display devices suffer from accommodation-vergence mismatches when displaying image information. Such mismatches may cause user discomfort and may make long-term wear of the device infeasible. Advantageously, display devices according to embodiments herein allow for long-term wear of the device by, among other things, providing a correct match between accommodation and vergence in the user. As a result, users of the device may be able to wear and use the device substantially continuously for durations of 3 hours or more, 4 hours or more, 5 hours or more, 6 hours or more, or all day, without removing the device for more than 25%, more than 20%, more than 15%, more than 10%, or more than 5% of the duration. In some embodiments, the display device may display augmented reality images substantially continuously for the above-noted durations.

Advantageously, the long-term wearability of a display device (e.g., due to the ability to provide a correct accommodation-vergence match) provides a platform that allows long-term and passive glucose testing to be performed. The testing may be performed regularly, or at an arbitrary time. Further, some embodiments may provide alerts when attention may be needed (e.g., when the determined glucose level and/or a parameter relating to glucose level falls outside a certain range).

The display devices and/or systems may also allow a user to monitor his or her glucose level over time. For example, the determined glucose levels from the glucose testing can be stored in the user-wearable display and/or system in a local database and/or in a remote database accessible to the user-wearable display and/or system. Thus, the display devices and/or systems may allow the gathering a relatively large amount of data. Because the display devices and/or systems may be worn for long durations, preferably, as the user is going about part or all of his or her daily life, the number and/or repetition of glucose testing may be higher than that obtained if the user is required to prick his or her finger. In some embodiments, the user-wearable devices and/or systems may compare a contemporaneous glucose level with historical glucose levels. The determined glucose level can also be individualized by calibration, e.g., with the glucose level obtained by blood testing.

Various embodiment described herein may also detect and track the user's physical state, activities and/or environmental conditions so that factors (e.g., the user's temperature, whether the user is fasting, sweating, or in an extreme temperature environment, etc.) that may affect the determined glucose level can be considered when evaluating the results to provide more accurate interpretations and assessments and/or to indicate whether an additional reading is recommended. In some embodiments, the user-wearable devices and/or systems may analyze the determined glucose levels and the tracked data for correlations, which may in some cases be used to provide a predictive model for future behavior. For example, when certain activities and/or conditions are detected (e.g., eating), the device and/or system may provide real time feedback such as alerts based on historical readings (e.g., an alert that the food the user is eating has historically resulted in higher glucose levels). As a result, various embodiments can aid users and doctors in maintaining a targeted blood sugar level by providing for better integrated diabetes/blood sugar management.

Figure 2:
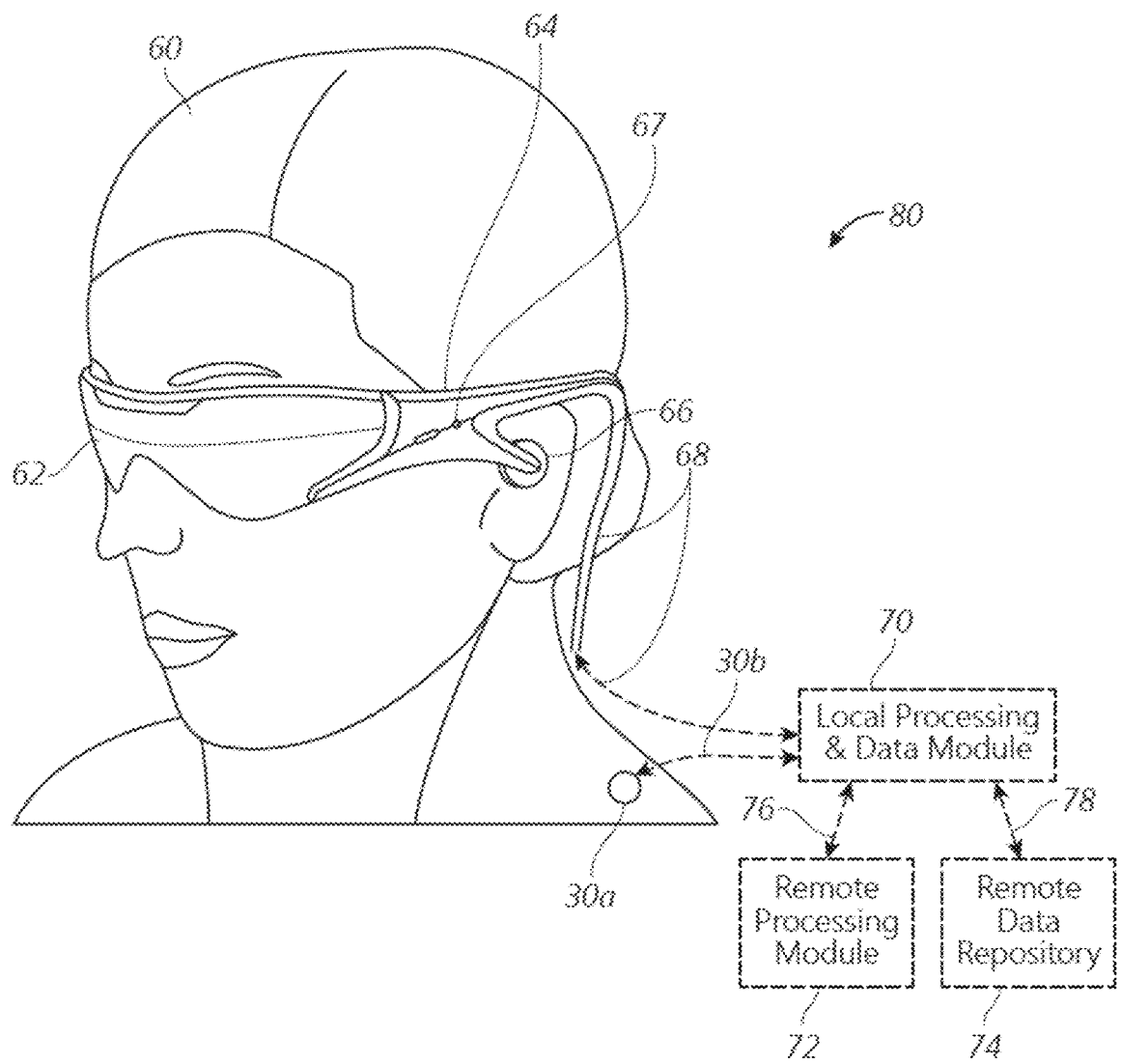
FIG. 2 illustrates an example of a wearable display system.

Reference is now made with FIG. 2. FIG. 2 illustrates an example of wearable display system 80. The display system 80 includes a display 62, and various mechanical and electronic modules and systems to support the functioning of that display 62. The display 62 may be coupled to a frame 64, which is wearable by a display system user or viewer 60 and which is configured to position the display 62 in front of the eyes of the user 60. The display 62 may be considered eyewear in some embodiments. In some embodiments, a speaker 66 is coupled to the frame 64 and positioned adjacent the ear canal of the user 60 (in some embodiments, another speaker, not shown, is positioned adjacent the other ear canal of the user to provide for stereo/shapeable sound control). In some embodiments, the display system may also include one or more microphones 67 or other devices to detect sound. In some embodiments, the microphone is configured to allow the user to provide inputs or commands to the system 80 (e.g., the selection of voice menu commands, natural language questions, etc.), and/or may allow audio communication with other persons (e.g., with other users of similar display systems. The microphone may further be configured as a peripheral sensor to continuously collect audio data (e.g., to passively collect from the user and/or environment). Such audio data may include user sounds such as heavy breathing, or environmental sounds, such as a loud bang indicative of a nearby event. The display system may also include a peripheral sensor 30*a*, which may be separate from the frame 64 and attached to the body of the user 60 (e.g., on the head, torso, an extremity, etc. of the user 60). The peripheral sensor 30*a* may be configured to acquire data regarding the user 60 in some embodiments, as described further herein.

With continued reference to FIG. 2, the display 62 is operatively coupled by communications link 68, such as by a wired lead or wireless connectivity, to a local data processing module 70 which may be mounted in a variety of configurations, such as fixedly attached to the frame 64, fixedly attached to a helmet or hat worn by the user, embedded in headphones, or otherwise removably attached to the user 60 (e.g., in a backpack-style configuration, in a belt-coupling style configuration). Similarly, the sensor 30*a* may be operatively coupled by communications link 30*b*, e.g., a wired lead or wireless connectivity, to the local processor and data module 70. The local processing and data module 70 may comprise a hardware processor, as well as digital memory, such as non-volatile memory (e.g., flash memory or hard disk drives), both of which may be utilized to assist in the processing, caching, and storage of data. The data include data a) captured from sensors (which may be, e.g., operatively coupled to the frame 64 or otherwise attached to the user 60), such as image capture devices (such as cameras), microphones, inertial measurement units, accelerometers, compasses, GPS units, radio devices, gyros, and/or other sensors disclosed herein; and/or b) acquired and/or processed using remote processing module 72 and/or remote data repository 74 (including data relating to virtual content), possibly for passage to the display 62 after such processing or retrieval. The local processing and data module 70 may be operatively coupled by communication links 76, 78, such as via a wired or wireless communication links, to the remote processing module 72 and remote data repository 74 such that these remote modules 72, 74 are operatively coupled to each other and available as resources to the local processing and data module 70. In some embodiments, the local processing and data module 70 may include one or more of the image capture devices, microphones, inertial measurement units, accelerometers, compasses, GPS units, radio devices, and/or gyros. In some other embodiments, one or more of these sensors may be attached to the frame 64, or may be standalone structures that communicate with the local processing and data module 70 by wired or wireless communication pathways.

With continued reference to FIG. 2, in some embodiments, the remote processing module 72 may comprise one or more processors configured to analyze and process data and/or image information. In some embodiments, the remote data repository 74 may comprise a digital data storage facility, which may be available through the internet or other networking configuration in a "cloud" resource configuration. In some embodiments, the remote data repository 74 may include one or more remote servers, which provide information, e.g., information for generating augmented reality content, to the local processing and data module 70 and/or the remote processing module 72. In some embodiments, all data is stored and all computations are performed in the local processing and data module, allowing fully autonomous use from a remote module.

Figure 3:
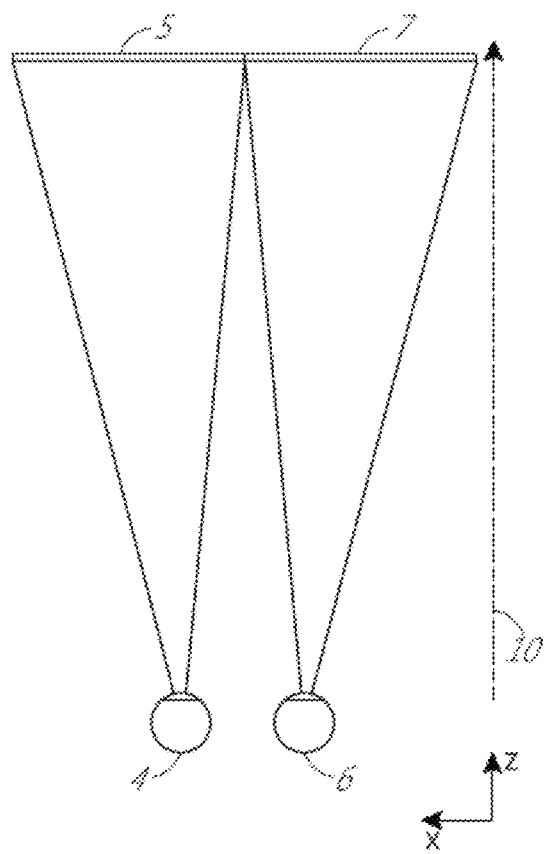
FIG. 3 illustrates a conventional display system for simulating three-dimensional imagery for a user.

The perception of an image as being "three-dimensional" or "3-D" may be achieved by providing slightly different presentations of the image to each eye of the viewer. FIG. 3 illustrates a conventional display system for simulating three-dimensional imagery for a user. Two distinct images 5, 7—one for each eye 4, 6—are outputted to the user. The images 5, 7 are spaced from the eyes 4, 6 by a distance 10 along an optical or z-axis parallel to the line of sight of the viewer. The images 5, 7 are flat and the eyes 4, 6 may focus on the images by assuming a single accommodated state. Such systems rely on the human visual system to combine the images 5, 7 to provide a perception of depth and/or scale for the combined image.

It will be appreciated, however, that the human visual system is more complicated and providing a realistic perception of depth is more challenging. For example, many viewers of conventional "3-D" display systems find such systems to be uncomfortable or may not perceive a sense of depth at all. Without being limited by theory, it is believed that viewers of an object may perceive the object as being "three-dimensional" due to a combination of vergence and accommodation. Vergence movements (i.e., rotation of the eyes so that the pupils move toward or away from each other to converge the lines of sight of the eyes to fixate upon an object) of the two eyes relative to each other are closely associated with focusing (or "accommodation") of the lenses and pupils of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex," as well as pupil dilation or constriction. Likewise, a change in vergence will trigger a matching change in accommodation of lens shape and pupil size, under normal conditions. As noted herein, many stereoscopic or "3-D" display systems display a scene using slightly different presentations (and, so, slightly different images) to each eye such that a three-dimensional perspective is perceived by the human visual system. Such systems are uncomfortable for many viewers, however, since they, among other things, simply provide a different presentation of a scene, but with the eyes viewing all the image information at a single accommodated state, and work against the "accommodation-vergence reflex." Display systems that provide a better match between accommodation and vergence may form more realistic and comfortable simulations of three-dimensional imagery contributing to increased duration of wear and in turn compliance to diagnostic and therapy protocols.

Figure 4:
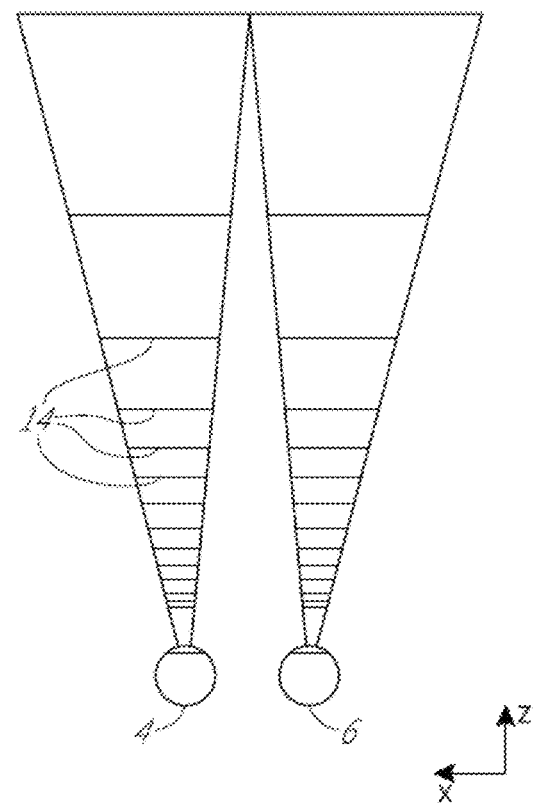
FIG. 4 illustrates aspects of an approach for simulating three-dimensional imagery using multiple depth planes.

FIG. 4 illustrates aspects of an approach for simulating three-dimensional imagery using multiple depth planes. With reference to FIG. 4, objects at various distances from eyes 4, 6 on the z-axis are accommodated by the eyes 4, 6 so that those objects are in focus. The eyes (4 and 6) assume particular accommodated states to bring into focus objects at different distances along the z-axis. Consequently, a particular accommodated state may be said to be associated with a particular one of depth planes 14, which has an associated focal distance, such that objects or parts of objects in a particular depth plane are in focus when the eye is in the accommodated state for that depth plane. In some embodiments, three-dimensional imagery may be simulated by providing different presentations of an image for each of the eyes 4, 6, and also by providing different presentations of the image corresponding to each of the depth planes. While shown as being separate for clarity of illustration, it will be appreciated that the fields of view of the eyes 4, 6 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state.

Figure 5A:
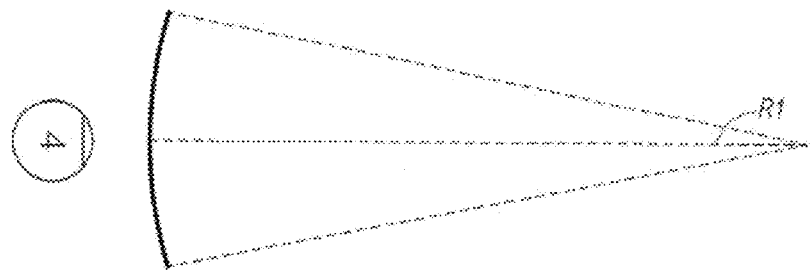
FIGS. 5A-5C illustrate relationships between radius of curvature and focal radius.
Figure 5B:
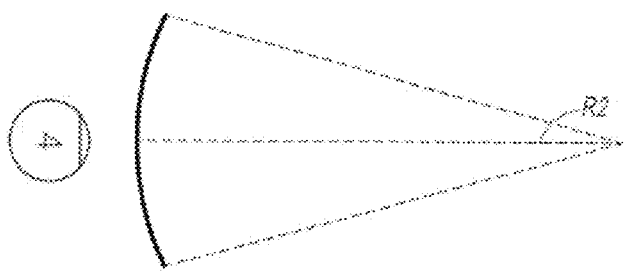
Figure 5C:
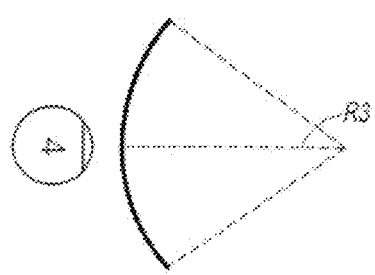

The distance between an object and the eye 4 or 6 may also change the amount of divergence of light from that object, as viewed by that eye. FIGS. 5A-5C illustrate relationships between distance and the divergence of light rays. The distance between the object and the eye 4 is represented by, in order of decreasing distance, R1, R2, and R3. As shown in FIGS. 5A-5C, the light rays become more divergent as distance to the object decreases. As distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 4. Consequently, at different depth planes, the degree of divergence of light rays is also different, with the degree of divergence increasing with decreasing distance between depth planes and the viewer's eye 4. While only a single eye 4 is illustrated for clarity of illustration in FIGS. 5A-5C and other figures herein, it will be appreciated that the discussions regarding eye 4 may be applied to both eyes 4 and 6 of a viewer.

Without being limited by theory, it is believed that the human eye typically can interpret a finite number of depth planes to provide depth perception. Consequently, a highly believable simulation of perceived depth may be achieved by providing, to the eye, different presentations of an image (e.g., scene) corresponding to each of these limited number of depth planes. The different presentations may be separately focused by the viewer's eyes, thereby helping to provide the user with depth cues based on the accommodation of the eye required to bring into focus different image features for the scene located on different depth plane and/or based on observing different image features on different depth planes being out of focus.

Figure 6:
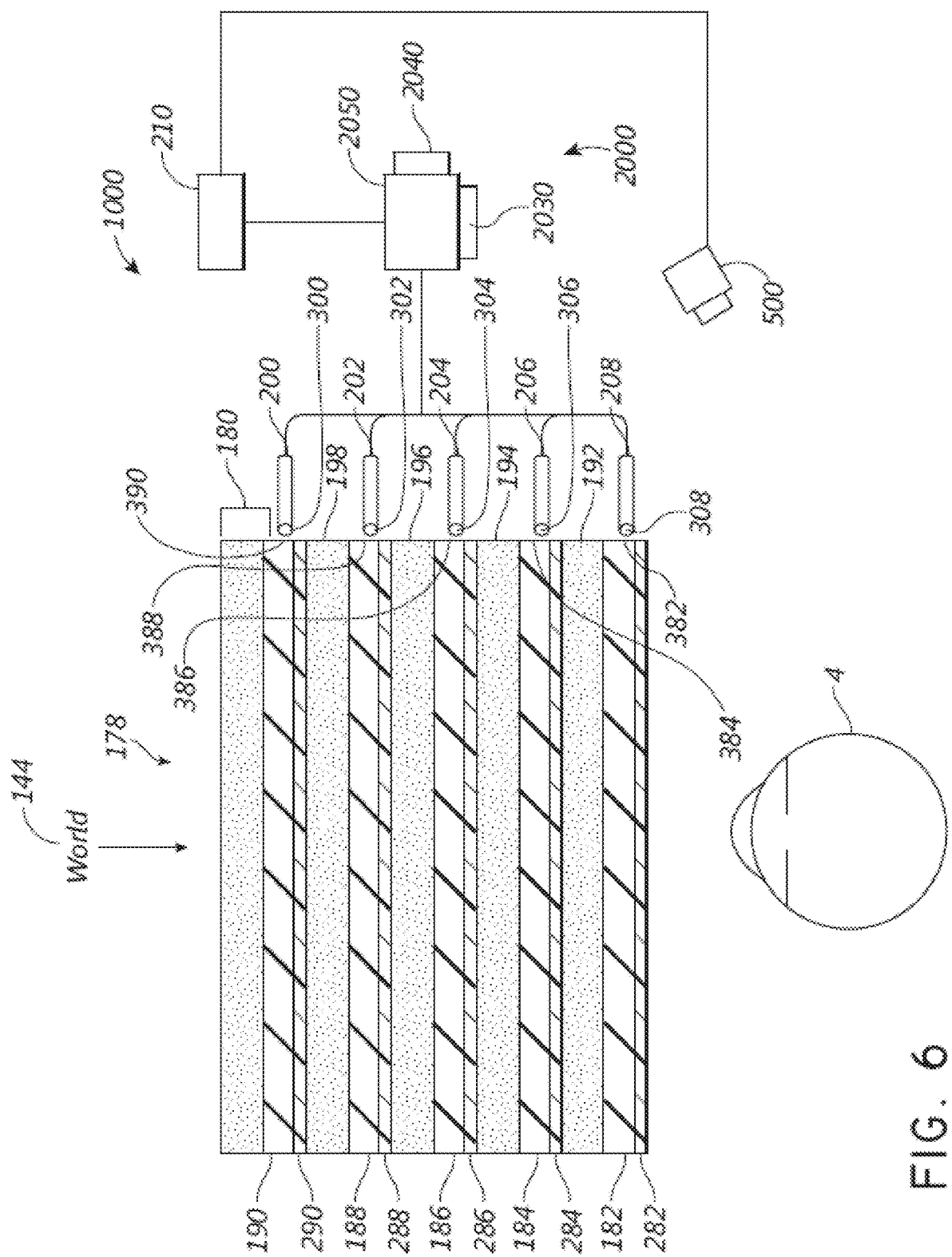
FIG. 6 illustrates an example of a waveguide stack for outputting image information to a user.

FIG. 6 illustrates an example of a waveguide stack for outputting image information to a user. A display system 1000 includes a stack of waveguides, or stacked waveguide assembly, 178 that may be utilized to provide three-dimensional perception to the eye/brain using a plurality of waveguides 182, 184, 186, 188, 190. In some embodiments, the display system 1000 is the system 80 of FIG. 2, with FIG. 6 schematically showing some parts of that system 80 in greater detail. For example, the waveguide assembly 178 may be part of the display 62 of FIG. 2. It will be appreciated that the display system 1000 may be considered a light field display in some embodiments.

With continued reference to FIG. 6, the waveguide assembly 178 may also include a plurality of features 198, 196, 194, 192 between the waveguides. In some embodiments, the features 198, 196, 194, 192 may be one or more lenses. The waveguides 182, 184, 186, 188, 190 and/or the plurality of lenses 198, 196, 194, 192 may be configured to send image information to the eye with various levels of wavefront curvature or light ray divergence. Each waveguide level may be associated with a particular depth plane and may be configured to output image information corresponding to that depth plane. Image injection devices 200, 202, 204, 206, 208 may function as a source of light for the waveguides and may be utilized to inject image information into the waveguides 182, 184, 186, 188, 190, each of which may be configured, as described herein, to distribute incoming light across each respective waveguide, for output toward the eye 4. Light exits an output surface 300, 302, 304, 306, 308 of the image injection devices 200, 202, 204, 206, 208 and is injected into a corresponding input surface 382, 384, 386, 388, 390 of the waveguides 182, 184, 186, 188, 190. In some embodiments, the each of the input surfaces 382, 384, 386, 388, 390 may be an edge of a corresponding waveguide, or may be part of a major surface of the corresponding waveguide (that is, one of the waveguide surfaces directly facing the world 144 or the viewer's eye 4). In some embodiments, a single beam of light (e.g. a collimated beam) may be injected into each waveguide to output an entire field of cloned collimated beams that are directed toward the eye 4 at particular angles (and amounts of divergence) corresponding to the depth plane associated with a particular waveguide. In some embodiments, a single one of the image injection devices 200, 202, 204, 206, 208 may be associated with and inject light into a plurality (e.g., three) of the waveguides 182, 184, 186, 188, 190.

In some embodiments, the image injection devices 200, 202, 204, 206, 208 are discrete displays that each produce image information for injection into a corresponding waveguide 182, 184, 186, 188, 190, respectively. In some other embodiments, the image injection devices 200, 202, 204, 206, 208 are the output ends of a single multiplexed display which may, e.g., pipe image information via one or more optical conduits (such as fiber optic cables) to each of the image injection devices 200, 202, 204, 206, 208. It will be appreciated that the image information provided by the image injection devices 200, 202, 204, 206, 208 may include light of different wavelengths, or colors (e.g., different component colors, as discussed herein).

In some embodiments, the light injected into the waveguides 182, 184, 186, 188, 190 is provided by a light projector system 2000, which comprises a light module 2040, which may include a light emitter, such as a light emitting diode (LED). The light from the light module 2040 may be directed to and modified by a light modulator 2030, e.g., a spatial light modulator, via a beam splitter 2050. The light modulator 2030 may be configured to change the perceived intensity of the light injected into the waveguides 182, 184, 186, 188, 190. Examples of spatial light modulators include liquid crystal displays (LCD) including a liquid crystal on silicon (LCOS) displays.

In some embodiments, the display system 1000 may be a scanning fiber display comprising one or more scanning fibers configured to project light in various patterns (e.g., raster scan, spiral scan, Lissajous patterns, etc.) into one or more waveguides 182, 184, 186, 188, 190 and ultimately to the eye 4 of the viewer. In some embodiments, the illustrated image injection devices 200, 202, 204, 206, 208 may schematically represent a single scanning fiber or a bundles of scanning fibers configured to inject light into one or a plurality of the waveguides 182, 184, 186, 188, 190. In some other embodiments, the illustrated image injection devices 200, 202, 204, 206, 208 may schematically represent a plurality of scanning fibers or a plurality of bundles of scanning, fibers each of which are configured to inject light into an associated one of the waveguides 182, 184, 186, 188, 190. It will be appreciated that the one or more optical fibers may be configured to transmit light from the light module 2040 to the one or more waveguides 182, 184, 186, 188, 190. It will be appreciated that one or more intervening optical structures may be provided between the scanning fiber, or fibers, and the one or more waveguides 182, 184, 186, 188, 190 to, e.g., redirect light exiting the scanning fiber into the one or more waveguides 182, 184, 186, 188, 190.

A controller 210 controls the operation of one or more of the stacked waveguide assembly 178, including operation of the image injection devices 200, 202, 204, 206, 208, the light source 2040, and the light modulator 2030. In some embodiments, the controller 210 is part of the local data processing module 70. The controller 210 includes programming (e.g., instructions in a non-transitory medium) that regulates the timing and provision of image information to the waveguides 182, 184, 186, 188, 190 according to, e.g., any of the various schemes disclosed herein. In some embodiments, the controller may be a single integral device, or a distributed system connected by wired or wireless communication channels. The controller 210 may be part of the processing modules 70 or 72 (FIG. 2) in some embodiments.

With continued reference to FIG. 6, the waveguides 182, 184, 186, 188, 190 may be configured to propagate light within each respective waveguide by total internal reflection (TIR). The waveguides 182, 184, 186, 188, 190 may each be planar or have another shape (e.g., curved), with major top and bottom surfaces and edges extending between those major top and bottom surfaces. In the illustrated configuration, the waveguides 182, 184, 186, 188, 190 may each include outcoupling optical elements 282, 284, 286, 288, 290 that are configured to extract light out of a waveguide by redirecting the light, propagating within each respective waveguide, out of the waveguide to output image information to the eye 4. Extracted light may also be referred to as outcoupled light and the outcoupling optical elements light may also be referred to light extracting optical elements. An extracted beam of light is outputted by the waveguide at locations at which the light propagating in the waveguide strikes a light extracting optical element. The outcoupling optical elements 282, 284, 286, 288, 290 may, for example, be gratings, including diffractive optical features, as discussed further herein. While illustrated disposed at the bottom major surfaces of the waveguides 182, 184, 186, 188, 190 for ease of description and drawing clarity, in some embodiments, the outcoupling optical elements 282, 284, 286, 288, 290 may be disposed at the top and/or bottom major surfaces, and/or may be disposed directly in the volume of the waveguides 182, 184, 186, 188, 190, as discussed further herein. In some embodiments, the outcoupling optical elements 282, 284, 286, 288, 290 may be formed in a layer of material that is attached to a transparent substrate to form the waveguides 182, 184, 186, 188, 190. In some other embodiments, the waveguides 182, 184, 186, 188, 190 may be a monolithic piece of material and the outcoupling optical elements 282, 284, 286, 288, 290 may be formed on a surface and/or in the interior of that piece of material.

With continued reference to FIG. 6, as discussed herein, each waveguide 182, 184, 186, 188, 190 is configured to output light to form an image corresponding to a particular depth plane. For example, the waveguide 182 nearest the eye may be configured to deliver collimated light, as injected into such waveguide 182, to the eye 4. The collimated light may be representative of the optical infinity focal plane. The next waveguide up 184 may be configured to send out collimated light which passes through the first lens 192 (e.g., a negative lens) before it can reach the eye 4; such first lens 192 may be configured to create a slight convex wavefront curvature so that the eye/brain interprets light coming from that next waveguide up 184 as coming from a first focal plane closer inward toward the eye 4 from optical infinity. Similarly, the third up waveguide 186 passes its output light through both the first 192 and second 194 lenses before reaching the eye 4; the combined optical power of the first 192 and second 194 lenses may be configured to create another incremental amount of wavefront curvature so that the eye/brain interprets light coming from the third waveguide 186 as coming from a second focal plane that is even closer inward toward the person from optical infinity than was light from the next waveguide up 184.

The other waveguide layers 188, 190 and lenses 196, 198 are similarly configured, with the highest waveguide 190 in the stack sending its output through all of the lenses between it and the eye for an aggregate focal power representative of the closest focal plane to the person. To compensate for the stack of lenses 198, 196, 194, 192 when viewing/interpreting light coming from the world 144 on the other side of the stacked waveguide assembly 178, a compensating lens layer 180 may be disposed at the top of the stack to compensate for the aggregate power of the lens stack 198, 196, 194, 192 below. Such a configuration provides as many perceived focal planes as there are available waveguide/lens pairings. Both the outcoupling optical elements of the waveguides and the focusing aspects of the lenses may be static (i.e., not dynamic or electro-active). In some alternative embodiments, either or both may be dynamic using electro-active features.

In some embodiments, two or more of the waveguides 182, 184, 186, 188, 190 may have the same associated depth plane. For example, multiple waveguides 182, 184, 186, 188, 190 may be configured to output images set to the same depth plane, or multiple subsets of the waveguides 182, 184, 186, 188, 190 may be configured to output images set to the same plurality of depth planes, with one set for each depth plane. This can provide advantages for forming a tiled image to provide an expanded field of view at those depth planes.

With continued reference to FIG. 6, the outcoupling optical elements 282, 284, 286, 288, 290 may be configured to both redirect light out of their respective waveguides and to output this light with the appropriate amount of divergence or collimation for a particular depth plane associated with the waveguide. As a result, waveguides having different associated depth planes may have different configurations of outcoupling optical elements 282, 284, 286, 288, 290, which output light with a different amount of divergence depending on the associated depth plane. In some embodiments, the light extracting optical elements 282, 284, 286, 288, 290 may be volumetric or surface features, which may be configured to output light at specific angles. For example, the light extracting optical elements 282, 284, 286, 288, 290 may be volume holograms, surface holograms, and/or diffraction gratings. In some embodiments, the features 198, 196, 194, 192 may not be lenses; rather, they may simply be spacers (e.g., cladding layers and/or structures for forming air gaps).

In some embodiments, the outcoupling optical elements 282, 284, 286, 288, 290 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 4 with each intersection of the DOE, while the rest continues to move through a waveguide via total internal reflection. The light carrying the image information is thus divided into a number of related exit beams that exit the waveguide at a multiplicity of locations and the result is a fairly uniform pattern of exit emission toward the eye 4 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 500 (e.g., a digital camera, including visible light and infrared light cameras) may be provided to capture images of the eye 4 and/or tissue around the eye 4 to, e.g., detect user inputs. As used herein, a camera may be any image capture device. In some embodiments, the camera assembly 500 may include an image capture device and a light source to project light (e.g., infrared light) to the eye, which may then be reflected by the eye and detected by the image capture device. In some embodiments, the camera assembly 500 may be attached to the frame 64 (FIG. 2) and may be in electrical communication with the processing modules 70 and/or 72, which may process image information from the camera assembly 500. In some embodiments, one camera assembly 500 may be utilized for each eye, to separately monitor each eye.

Figure 7:
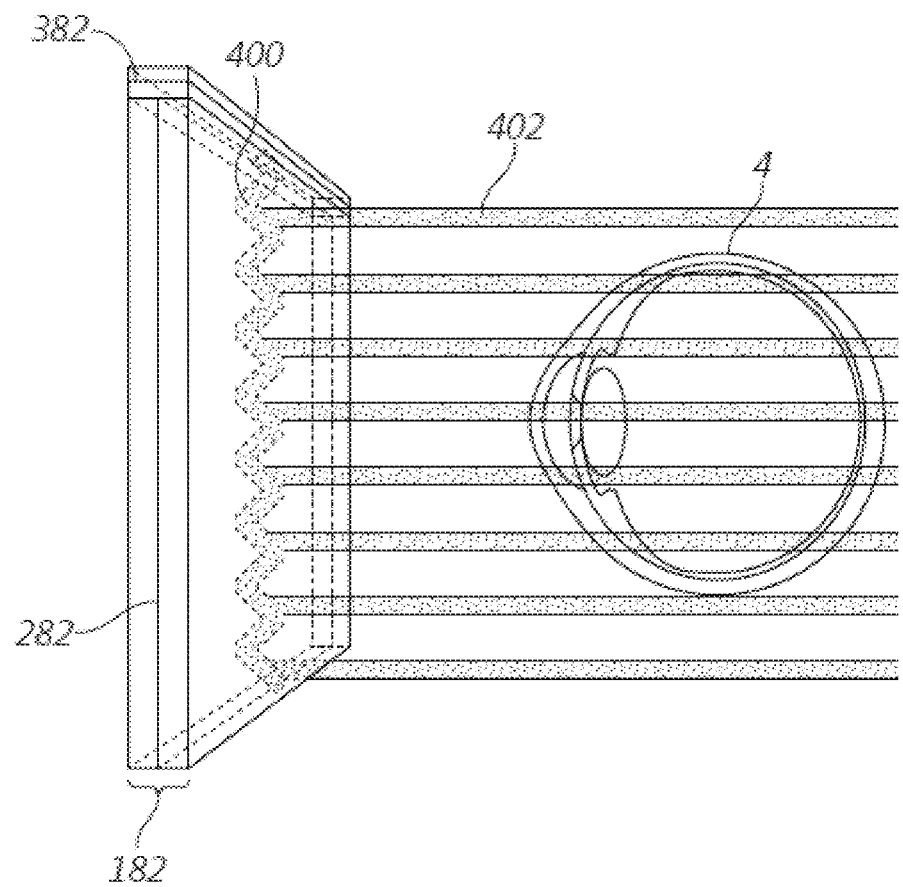
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 178 (FIG. 6) may function similarly, where the waveguide assembly 178 includes multiple waveguides. Light 400 is injected into the waveguide 182 at the input surface 382 of the waveguide 182 and propagates within the waveguide 182 by TIR. At points where the light 400 impinges on the DOE 282, a portion of the light exits the waveguide as exit beams 402. The exit beams 402 are illustrated as substantially parallel but, as discussed herein, they may also be redirected to propagate to the eye 4 at an angle (e.g., forming divergent exit beams), depending on the depth plane associated with the waveguide 182. It will be appreciated that substantially parallel exit beams may be indicative of a waveguide with outcoupling optical elements that outcouple light to form images that appear to be set on a depth plane at a large distance (e.g., optical infinity) from the eye 4. Other waveguides or other sets of outcoupling optical elements may output an exit beam pattern that is more divergent, which would require the eye 4 to accommodate to a closer distance to bring it into focus on the retina and would be interpreted by the brain as light from a distance closer to the eye 4 than optical infinity.

Figure 8:
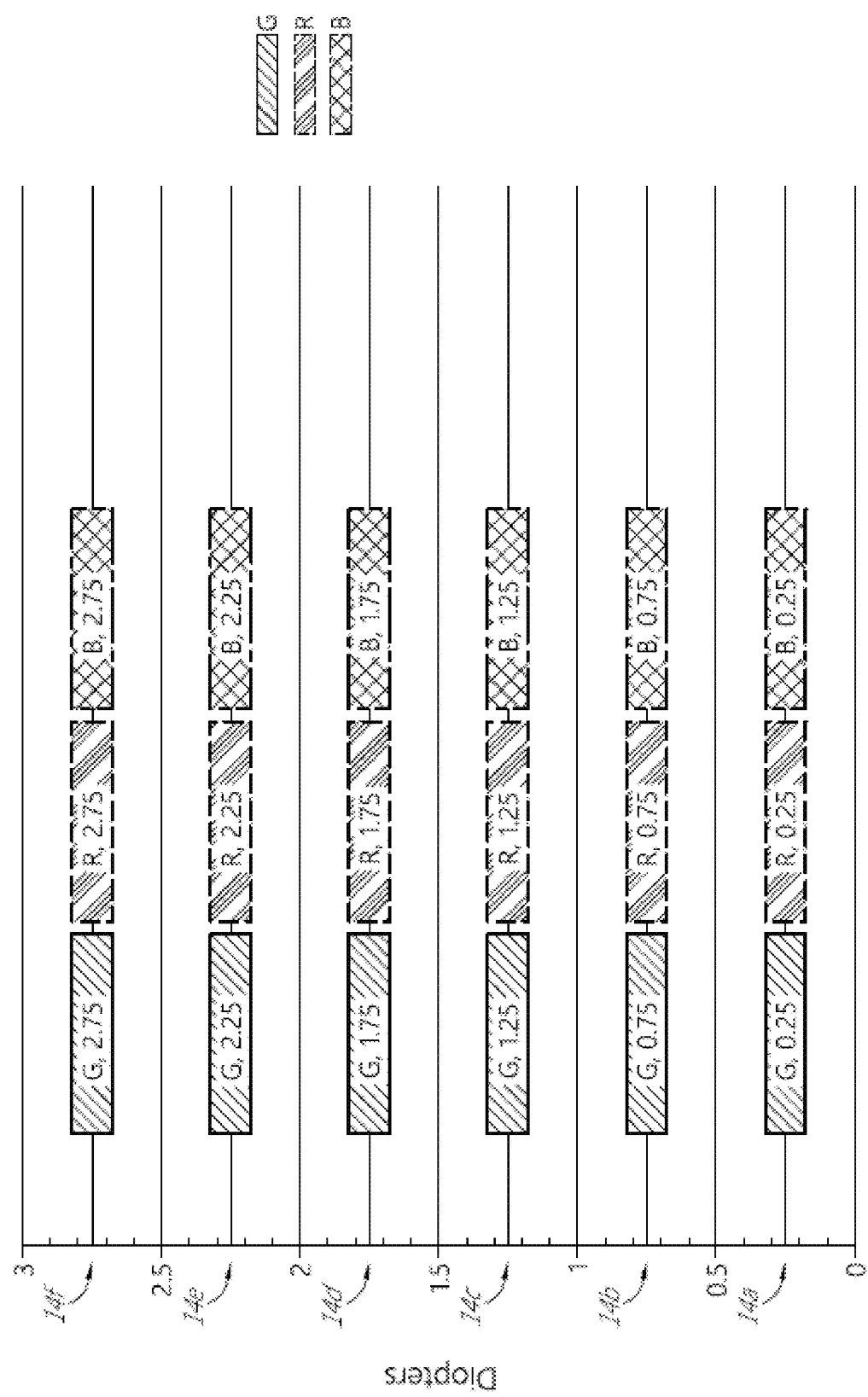
FIG. 8 illustrates an example of a stacked waveguide assembly in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 14*a*-14*f*, although more or fewer depths are also contemplated. Each depth plane may have three component color images associated with it: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue. In some embodiments, features 198, 196, 194, and 192 may be active or passive optical filters configured to block or selectively light from the ambient environment to the viewer's eyes.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 2040 (FIG. 6) may be configured to emit light of one or more wavelengths outside the visual perception range of the viewer, for example, infrared and/or ultraviolet wavelengths. In addition, the incoupling, outcoupling, and other light redirecting structures of the waveguides of the display 1000 may be configured to direct and emit this light out of the display towards the user's eye 4, e.g., for imaging and/or other applications.

Figure 9A:
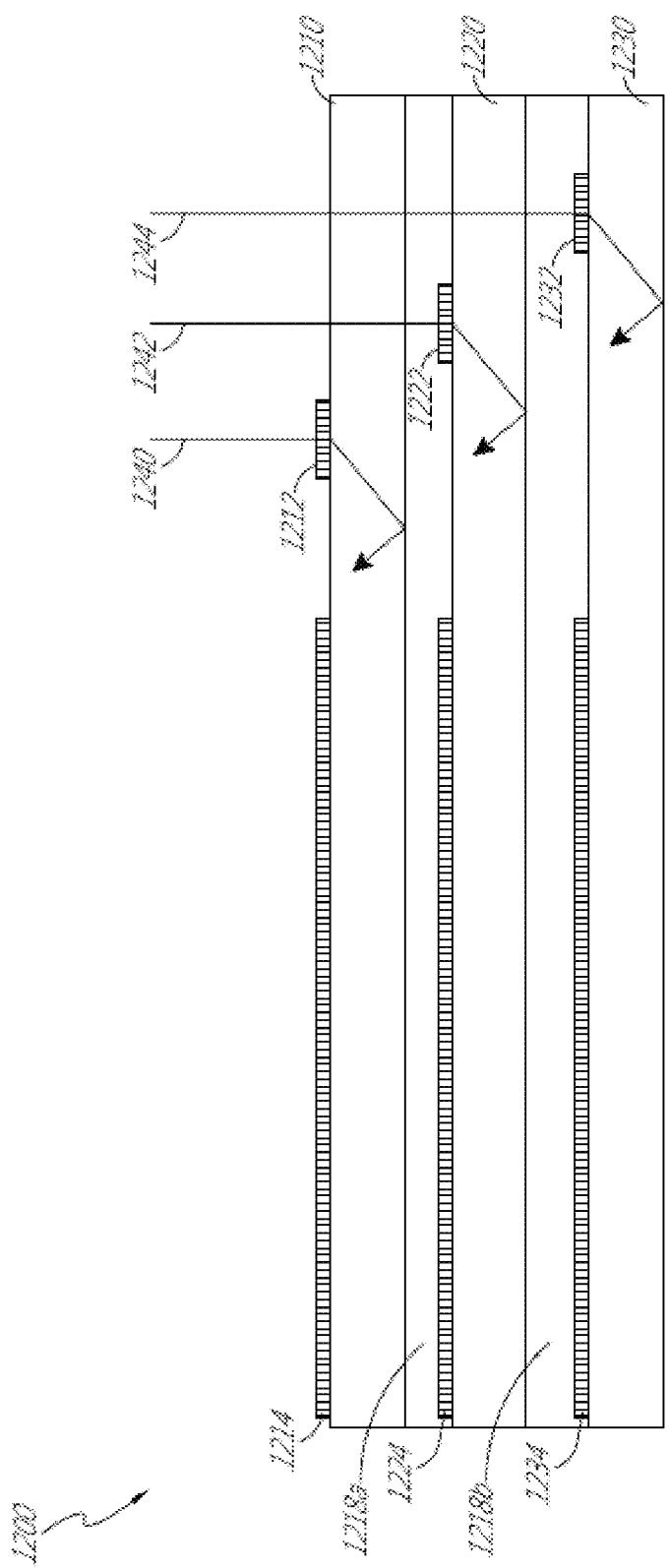
FIG. 9A illustrates a cross-sectional side view of an example of a set of stacked waveguides that each includes an in-coupling optical element.

With reference now to FIG. 9A, in some embodiments, light impinging on a waveguide may need to be redirected to incouple that light into the waveguide. An incoupling optical element may be used to redirect and incouple the light into its corresponding waveguide. FIG. 9A illustrates a cross-sectional side view of an example of a plurality or set 1200 of stacked waveguides that each includes an incoupling optical element. The waveguides may each be configured to output light of one or more different wavelengths, or one or more different ranges of wavelengths. It will be appreciated that the stack 1200 may correspond to the stack 178 (FIG. 6) and the illustrated waveguides of the stack 1200 may correspond to part of the plurality of waveguides 182, 184, 186, 188, 190, except that light from one or more of the image injection devices 200, 202, 204, 206, 208 is injected into the waveguides from a position that requires light to be redirected for incoupling.

The illustrated set 1200 of stacked waveguides includes waveguides 1210, 1220, and 1230. Each waveguide includes an associated incoupling optical element (which may also be referred to as a light input area on the waveguide), with, e.g., incoupling optical element 1212 disposed on a major surface (e.g., an upper major surface) of waveguide 1210, incoupling optical element 1224 disposed on a major surface (e.g., an upper major surface) of waveguide 1220, and incoupling optical element 1232 disposed on a major surface (e.g., an upper major surface) of waveguide 1230. In some embodiments, one or more of the incoupling optical elements 1212, 1222, 1232 may be disposed on the bottom major surface of the respective waveguide 1210, 1220, 1230 (particularly where the one or more incoupling optical elements are reflective, deflecting optical elements). As illustrated, the incoupling optical elements 1212, 1222, 1232 may be disposed on the upper major surface of their respective waveguide 1210, 1220, 1230 (or the top of the next lower waveguide), particularly where those incoupling optical elements are transmissive, deflecting optical elements. In some embodiments, the incoupling optical elements 1212, 1222, 1232 may be disposed in the body of the respective waveguide 1210, 1220, 1230. In some embodiments, as discussed herein, the incoupling optical elements 1212, 1222, 1232 are wavelength selective, such that they selectively redirect one or more wavelengths of light, while transmitting other wavelengths of light. While illustrated on one side or corner of their respective waveguide 1210, 1220, 1230, it will be appreciated that the incoupling optical elements 1212, 1222, 1232 may be disposed in other areas of their respective waveguide 1210, 1220, 1230 in some embodiments.

As illustrated, the incoupling optical elements 1212, 1222, 1232 may be laterally offset from one another. In some embodiments, each incoupling optical element may be offset such that it receives light without that light passing through another incoupling optical element. For example, each incoupling optical element 1212, 1222, 1232 may be configured to receive light from a different image injection device 200, 202, 204, 206, and 208 as shown in FIG. 6, and may be separated (e.g., laterally spaced apart) from other incoupling optical elements 1212, 1222, 1232 such that it substantially does not receive light from the other ones of the incoupling optical elements 1212, 1222, 1232.

Each waveguide also includes associated light distributing elements, with, e.g., light distributing elements 1214 disposed on a major surface (e.g., a top major surface) of waveguide 1210, light distributing elements 1224 disposed on a major surface (e.g., a top major surface) of waveguide 1220, and light distributing elements 1234 disposed on a major surface (e.g., a top major surface) of waveguide 1230. In some other embodiments, the light distributing elements 1214, 1224, 1234, may be disposed on a bottom major surface of associated waveguides 1210, 1220, 1230, respectively. In some other embodiments, the light distributing elements 1214, 1224, 1234, may be disposed on both top and bottom major surface of associated waveguides 1210, 1220, 1230, respectively; or the light distributing elements 1214, 1224, 1234, may be disposed on different ones of the top and bottom major surfaces in different associated waveguides 1210, 1220, 1230, respectively.

The waveguides 1210, 1220, 1230 may be spaced apart and separated by, e.g., gas, liquid, and/or solid layers of material. For example, as illustrated, layer 1218a may separate waveguides 1210 and 1220; and layer 1218b may separate waveguides 1220 and 1230. In some embodiments, the layers 1218a and 1218b are formed of low refractive index materials (that is, materials having a lower refractive index than the material forming the immediately adjacent one of waveguides 1210, 1220, 1230). Preferably, the refractive index of the material forming the layers 1218a, 1218b is 0.05 or more, or 0.10 or more less than the refractive index of the material forming the waveguides 1210, 1220, 1230. Advantageously, the lower refractive index layers 1218a, 1218b may function as cladding layers that facilitate total internal reflection (TIR) of light through the waveguides 1210, 1220, 1230 (e.g., TIR between the top and bottom major surfaces of each waveguide). In some embodiments, the layers 1218a, 1218b are formed of air. While not illustrated, it will be appreciated that the top and bottom of the illustrated set 1200 of waveguides may include immediately neighboring cladding layers.

Preferably, for ease of manufacturing and other considerations, the material forming the waveguides 1210, 1220, 1230 are similar or the same, and the material forming the layers 1218a, 1218b are similar or the same. In some embodiments, the material forming the waveguides 1210, 1220, 1230 may be different between one or more waveguides, and/or the material forming the layers 1218a, 1218b may be different, while still holding to the various refractive index relationships noted above.

With continued reference to FIG. 9A, light rays 1240, 1242, 1244 are incident on the set 1200 of waveguides. It will be appreciated that the light rays 1240, 1242, 1244 may be injected into the waveguides 1210, 1220, 1230 by one or more image injection devices 200, 202, 204, 206, 208 (FIG. 6).

In some embodiments, the light rays 1240, 1242, 1244 have different properties, e.g., different wavelengths or different ranges of wavelengths, which may correspond to different colors. The incoupling optical elements 1212, 1222, 1232 each deflect the incident light such that the light propagates through a respective one of the waveguides 1210, 1220, 1230 by TIR.

For example, incoupling optical element 1212 may be configured to deflect ray 1240, which has a first wavelength or range of wavelengths. Similarly, the transmitted ray 1242 impinges on and is deflected by the incoupling optical element 1222, which is configured to deflect light of a second wavelength or range of wavelengths. Likewise, the ray 1244 is deflected by the incoupling optical element 1232, which is configured to selectively deflect light of third wavelength or range of wavelengths.

With continued reference to FIG. 9A, the deflected light rays 1240, 1242, 1244 are deflected so that they propagate through a corresponding waveguide 1210, 1220, 1230; that is, the incoupling optical elements 1212, 1222, 1232 of each waveguide deflects light into that corresponding waveguide 1210, 1220, 1230 to incouple light into that corresponding waveguide. The light rays 1240, 1242, 1244 are deflected at angles that cause the light to propagate through the respective waveguide 1210, 1220, 1230 by TIR. The light rays 1240, 1242, 1244 propagate through the respective waveguide 1210, 1220, 1230 by TIR until impinging on the waveguide's corresponding light distributing elements 1214, 1224, 1234.

Figure 9B:
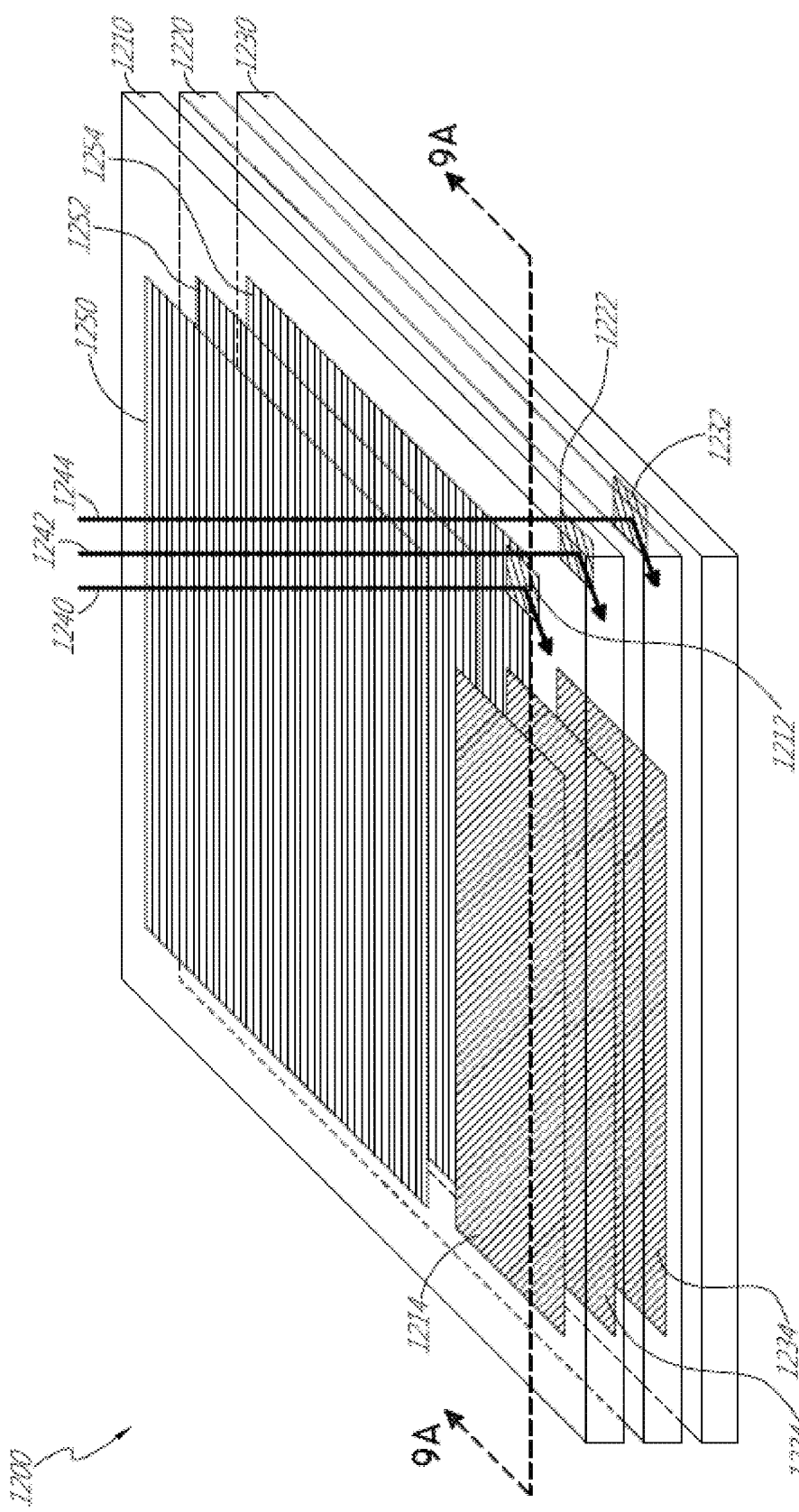
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the incoupled light rays 1240, 1242, 1244, are deflected by the incoupling optical elements 1212, 1222, 1232, respectively, and then propagate by TIR within the waveguides 1210, 1220, 1230, respectively. The light rays 1240, 1242, 1244 then impinge on the light distributing elements 1214, 1224, 1234, respectively. The light distributing elements 1214, 1224, 1234 deflect the light rays 1240, 1242, 1244 so that they propagate towards the outcoupling optical elements 1250, 1252, 1254, respectively.

In some embodiments, the light distributing elements 1214, 1224, 1234 are orthogonal pupil expanders (OPE's). In some embodiments, the OPE's both deflect or distribute light to the outcoupling optical elements 1250, 1252, 1254 and also increase the beam or spot size of this light as it propagates to the outcoupling optical elements. In some embodiments, e.g., where the beam size is already of a desired size, the light distributing elements 1214, 1224, 1234 may be omitted and the incoupling optical elements 1212, 1222, 1232 may be configured to deflect light directly to the outcoupling optical elements 1250, 1252, 1254. For example, with reference to FIG. 9A, the light distributing elements 1214, 1224, 1234 may be replaced with outcoupling optical elements 1250, 1252, 1254, respectively. In some embodiments, the outcoupling optical elements 1250, 1252, 1254 are exit pupils (EP's) or exit pupil expanders (EPE's) that direct light in a viewer's eye 4 (FIG. 7).

Accordingly, with reference to FIGS. 9A and 9B, in some embodiments, the set 1200 of waveguides includes waveguides 1210, 1220, 1230; incoupling optical elements 1212, 1222, 1232; light distributing elements (e.g., OPE's) 1214, 1224, 1234; and outcoupling optical elements (e.g., EP's) 1250, 1252, 1254 for each component color. The waveguides 1210, 1220, 1230 may be stacked with an air gap/cladding layer between each one. The incoupling optical elements 1212, 1222, 1232 redirect or deflect incident light (with different incoupling optical elements receiving light of different wavelengths) into its waveguide. The light then propagates at an angle which will result in TIR within the respective waveguide 1210, 1220, 1230. In the example shown, light ray 1240 (e.g., blue light) is deflected by the first incoupling optical element 1212, and then continues to bounce down the waveguide, interacting with the light distributing element (e.g., OPE's) 1214 and then the outcoupling optical element (e.g., EPs) 1250, in a manner described earlier. The light rays 1242 and 1244 (e.g., green and red light, respectively) will pass through the waveguide 1210, with light ray 1242 impinging on and being deflected by incoupling optical element 1222. The light ray 1242 then bounces down the waveguide 1220 via TIR, proceeding on to its light distributing element (e.g., OPEs) 1224 and then the outcoupling optical element (e.g., EP's) 1252. Finally, light ray 1244 (e.g., red light) passes through the waveguide 1220 to impinge on the light incoupling optical elements 1232 of the waveguide 1230. The light incoupling optical elements 1232 deflect the light ray 1244 such that the light ray propagates to light distributing element (e.g., OPEs) 1234 by TIR, and then to the outcoupling optical element (e.g., EPs) 1254 by TIR. The outcoupling optical element 1254 then finally outcouples the light ray 1244 to the viewer, who also receives the outcoupled light from the other waveguides 1210, 1220.

Figure 9C:
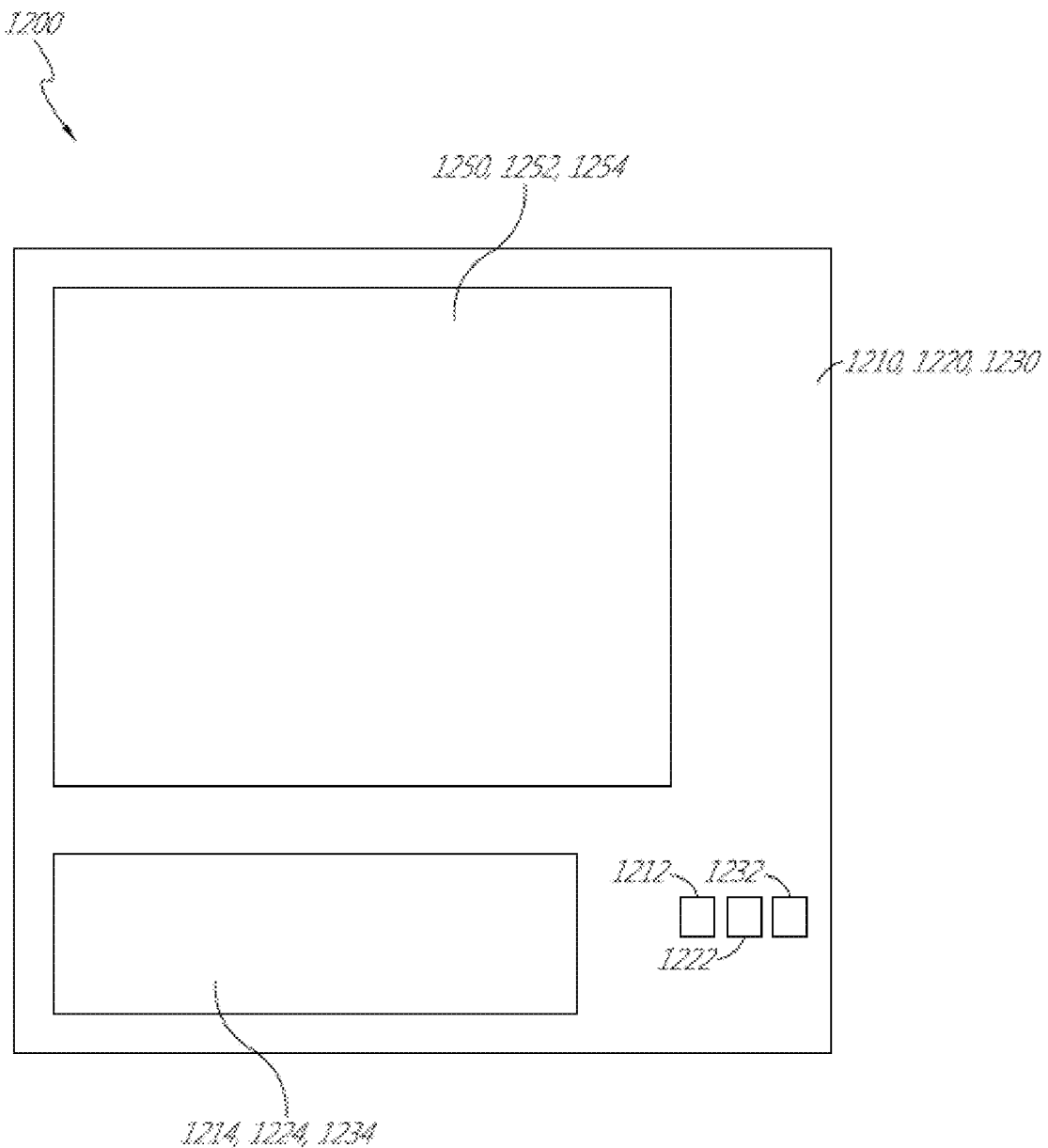
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 1210, 1220, 1230, along with each waveguide's associated light distributing element 1214, 1224, 1234 and associated outcoupling optical element 1250, 1252, 1254, may be vertically aligned. However, as discussed herein, the incoupling optical elements 1212, 1222, 1232 are not vertically aligned; rather, the incoupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated incoupling optical elements may be referred to as a shifted pupil system, and the in coupling optical elements within these arrangements may correspond to sub pupils.

Figure 10:
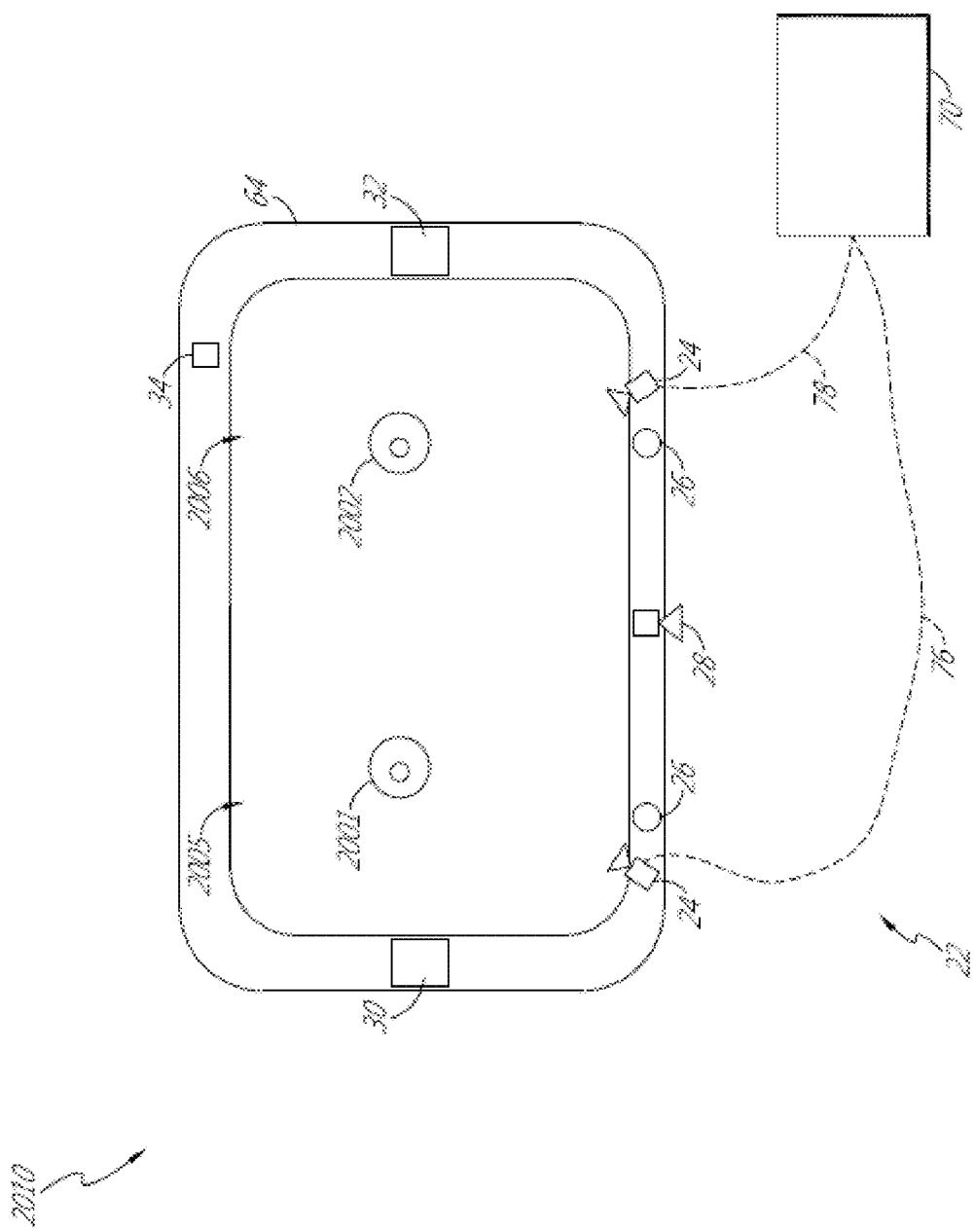
FIG. 10 shows a schematic view of an example of various components of an augmented reality system comprising environmental and user sensors.

With reference now to FIG. 10, which shows a schematic view of an example of various components of an augmented reality display system comprising user sensors 24, 28, 30, 32 and environmental sensors 34. In some embodiments, the augmented reality display system may be a mixed reality display system. As shown, the user sensors 24, 28, 30, 32 may be configured to detect data regarding the user, and the environmental sensors 34 may be configured to collect data regarding parameters external to the user. In some embodiments, the display system may be configured to store data related to and/or characterizing AR content delivered to the user (e.g., the time, location, color make-up, sound volume etc., of the AR content).

The user sensors will be discussed first. As illustrated, an augmented reality display system 2010 may include various user sensors. The augmented reality display system 2010 may correspond to the system 80 of FIG. 2 and may include a viewer imaging system 22. The system 22 may include cameras 24 (e.g., infrared, UV, and/or visible light cameras) paired with light sources 26 (e.g., infrared light sources) directed at and configured to monitor the user (e.g., the eyes 2001, 2002 and/or surrounding tissues of the user). The cameras 24 and light sources 26 may be operatively coupled to the local processing module 70. Such cameras 24 may be configured to monitor one or more of the orientation, shape, and symmetry of pupils (including pupil sizes) or irises of the respective eyes, and/or tissues surrounding the eye, such as eyelids or eyebrows to conduct the various analyses disclosed herein. In some embodiments, imaging of the iris and/or retina of an eye may be used for secure identification of a user.

With continued reference to FIG. 10, cameras 24 may further be configured to image the retinas of the respective eyes, such as for diagnostic purposes and/or for orientation tracking based on the location of retinal features, such as the fovea or features of the fundus. Iris and retina imaging or scanning may be performed for secure identification of users for, e.g., correctly associating user data with a particular user and/or to present private information to the appropriate user. In some embodiments, in addition to or as an alternative to the cameras 24, one or more cameras 28 may be configured to detect and/or monitor various other aspects of the status of a user. For example, one or more cameras 28 may be inward-facing and configured to monitor the shape, position, movement, color, and/or other properties of features other than the eyes of the user, e.g., one or more facial features (e.g., facial expression, voluntary movement, involuntary tics). In another example, one or more cameras 28 may be downward-facing and configured to monitor the position, movement, and/or other features or properties of the arms, hands, legs, feet, and/or torso of a user.

In some embodiments, as disclosed herein, the display system 2010 may include a spatial light modulator that variably projects, through a fiber scanner (e.g., the image injection devices in FIGS. 6-200, 202, 204, 206, 208), light beams across the retina of the user to form an image. In some embodiments, the fiber scanner may be used in conjunction with, or in place of, the cameras 24 or 28 to, e.g., track or image the user's eyes. For example, as an alternative to or in addition to the scanning fiber being configured to output light, the health system may have a separate light-receiving device to receive light reflected from the user's eyes, and to collect data associated with that reflected light.

With continued reference to FIG. 10, the cameras 24, 28 and light sources 26 may be mounted on the frame 64, which may also hold the waveguide stacks 2005, 2006. In some embodiments, sensors and/or other electronic devices (e.g., the cameras 24, 28 and light sources 26) of the display system 2010 may be configured to communicate with the local processing and data module 70 through communication links 76, 70.

In some embodiments, in addition to providing data regarding the user, one or both of the cameras 24 and 28 may be utilized to track the eyes to provide user input. For example, the viewer imaging system 22 may be utilized to select items on virtual menus, and/or provide other input to the display system 2010, such as for providing user responses in the various tests and analyses disclosed herein.

In some embodiments, the display system 2010 may include motion sensors 32, such as one or more accelerometers, gyros, gesture sensors, gait sensors, balance sensors, and/or IMU sensors. The sensors 30 may include one or more inwardly directed (user directed) microphones configured to detect sounds, and various properties of those sound, including the intensity and type of sounds detected, the presence of multiple signals, and/or signal location.

The sensors 30 are schematically illustrated as being connected to the frame 64. It will be appreciated that this connection may take the form of a physical attachment to the frame 64 and may be anywhere on the frame 64, including the ends of the temples of the frame 64 which extend over the user's ears. For example, the sensors 30 may be mounted at the ends of the temples of the frame 64, at a point of contact between the frame 64 and the user. In some other embodiments, the sensors 30 may extend away from the frame 64 to contact the user 60 (FIG. 2). In yet other embodiments, the sensors 30 may not be physically attached to the frame 64; rather, the sensors 30 may take the form of peripheral sensors 30a (FIG. 2), which may be spaced apart from the frame 64.

In some embodiments, the display system 2010 may further include one or more environmental sensors 34 configured to detect objects, stimuli, people, animals, locations, or other aspects of the world around the user. For example, environmental sensors 34 may include one or more cameras, altimeters, barometers, chemical sensors, humidity sensors, temperature sensors, external microphones, light sensors (e.g., light meters), timing devices (e.g., clocks or calendars), or any combination or subcombination thereof. In some embodiments, multiple (e.g., two) microphones may be spaced-apart, to facilitate sound source location determinations. In various embodiments including environment sensing cameras, cameras may be located, for example, facing outward so as to capture images similar to at least a portion of an ordinary field of view of a user. Environmental sensors may further include emissions devices configured to receive signals such as laser, visible light, invisible wavelengths of light, sound (e.g., audible sound, ultrasound, or other frequencies). In some embodiments, one or more environmental sensors (e.g., cameras or light sensors) may be configured to measure the ambient light (e.g., luminance) of the environment (e.g., to capture the lighting conditions of the environment). Physical contact sensors, such as strain gauges, curb feelers, or the like, may also be included as environmental sensors.

In some embodiments, the display system 2010 may further be configured to receive other environmental inputs, such as GPS location data, weather data, date and time, or other available environmental data which may be received from the internet, satellite communication, or other suitable wired or wireless data communication method. The processing module 70 may be configured to access further information characterizing a location of the user, such as pollen count, demographics, air pollution, environmental toxins, information from smart thermostats, lifestyle statistics, or proximity to other users, buildings, or a healthcare provider. In some embodiments, information characterizing the location may be accessed using cloud-based or other remote databases. The processing module 70 may be configured to obtain such data and/or to further analyze data from any one or combinations of the environmental sensors.

The display system 2010 may be configured to collect and store data obtained through any of the sensors and/or inputs described above for extended periods of time. Data received at the device may be processed and/or stored at the local processing module 70 and/or remotely (e.g., as shown in FIG. 2, at the remote processing module 72 or remote data repository 74). In some embodiments, additional data, such as date and time, GPS location, or other global data may be received directly at the local processing module 70. Data regarding content being delivered to the user by the system, such as images, other visual content, or auditory content, may be received at the local processing module 70 as well.

Delivering Polarized Light for Determining Glucose Level

In one or more embodiments, augmented reality or virtual reality devices, systems, and/or methods may be configured to deliver polarized light and such that the glucose level of the user can be determined. Referring back to FIGS. 2, 6, and 10, various embodiments may be implemented by configuring a user wearable device and/or system 80, 1000, and/or 2010 with one or more additional components. For example, as disclosed herein, a polarized light source and a light analyzer can be incorporated into certain embodiments of user-wearable devices to deliver polarized light and such that the user's glucose level can be determined. In some embodiments, user-wearable devices can incorporate one or more user sensors to collect data regarding the user and/or one or more environmental sensors to collect data regarding the user's environment. Information from some such sensors can be used such that more accurate assessments of glucose levels can be determined. In some embodiments, user-wearable devices can also incorporate a processor (e.g., processing electronics in some instances) configured to determine the user's glucose level and/or to store and access information relating to the user's glucose level. User-wearable devices as described herein can advantageously provide improved devices, systems, and methods for determining and tracking a user's glucose level without drawing blood.

As described herein, the aqueous humor of the eye includes glucose molecules. Glucose molecules can cause the polarization angle of linearly polarized light to rotate as the light transmits through the molecules. The amount of polarization angle rotation can be related to the glucose level. In some instances, the greater the polarization angle rotation, the greater the glucose level and/or the lesser the polarization angle rotation, the lesser the glucose level. In some instances, the amount of polarization angle rotation can be proportional to the glucose concentration. As an example, the amount of polarization angle rotation can be directly proportional to the glucose concentration. Various embodiments described herein can include a polarized light source and a light analyzer. The light source can be configured to emit polarized light towards the eye of the user. In some embodiments, the light source can be configured to emit polarized light towards a specific area of the eye (e.g., at the vasculature in the retina). Some of the polarized light can reflect from the eye, and the light analyzer can measure the polarization angle rotation of the reflected light. The measured amount of the angle rotation can be used to determine the glucose level of the user. A polarization controller may be used to induce rotation of the polarization angle or the polarization of the light to determine how much polarization rotation was introduced by the glucose.

Figure 11A:
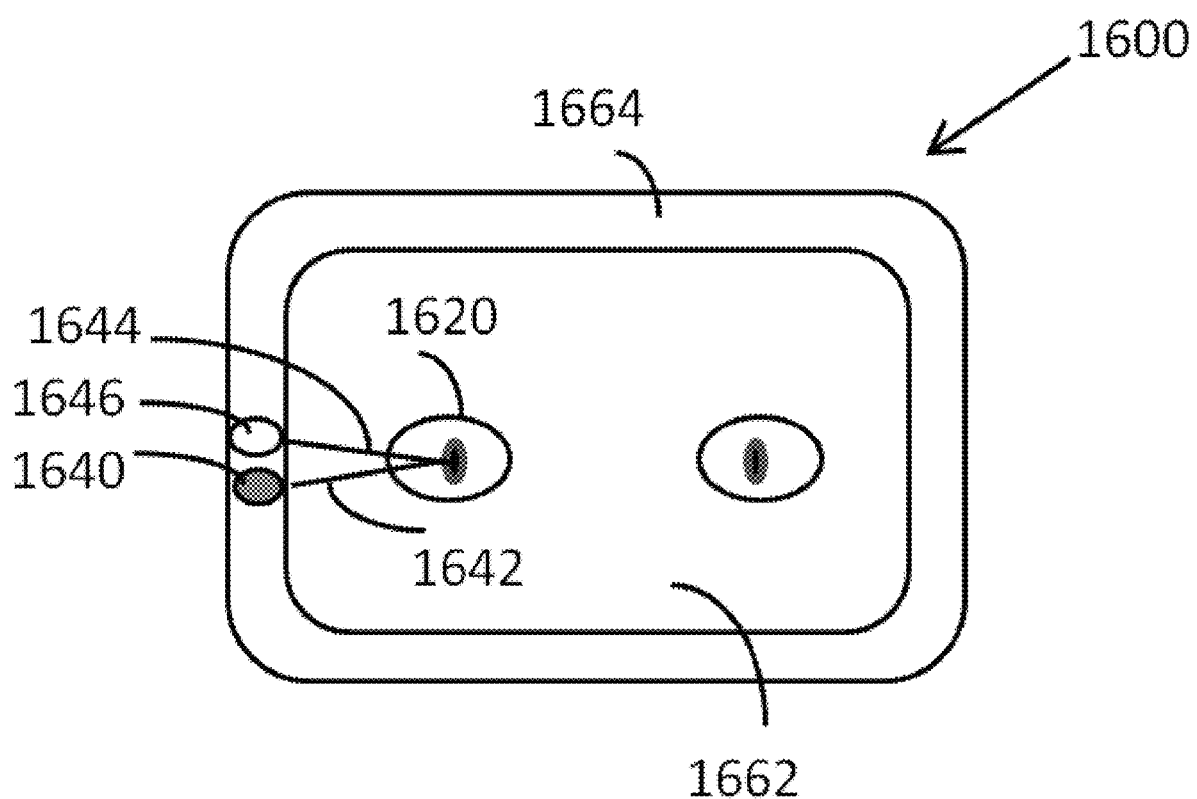
FIGS. 11A-11B illustrate a schematic view of an example augmented reality display device comprising a source of polarized light and a light analyzer.
Figure 11B:
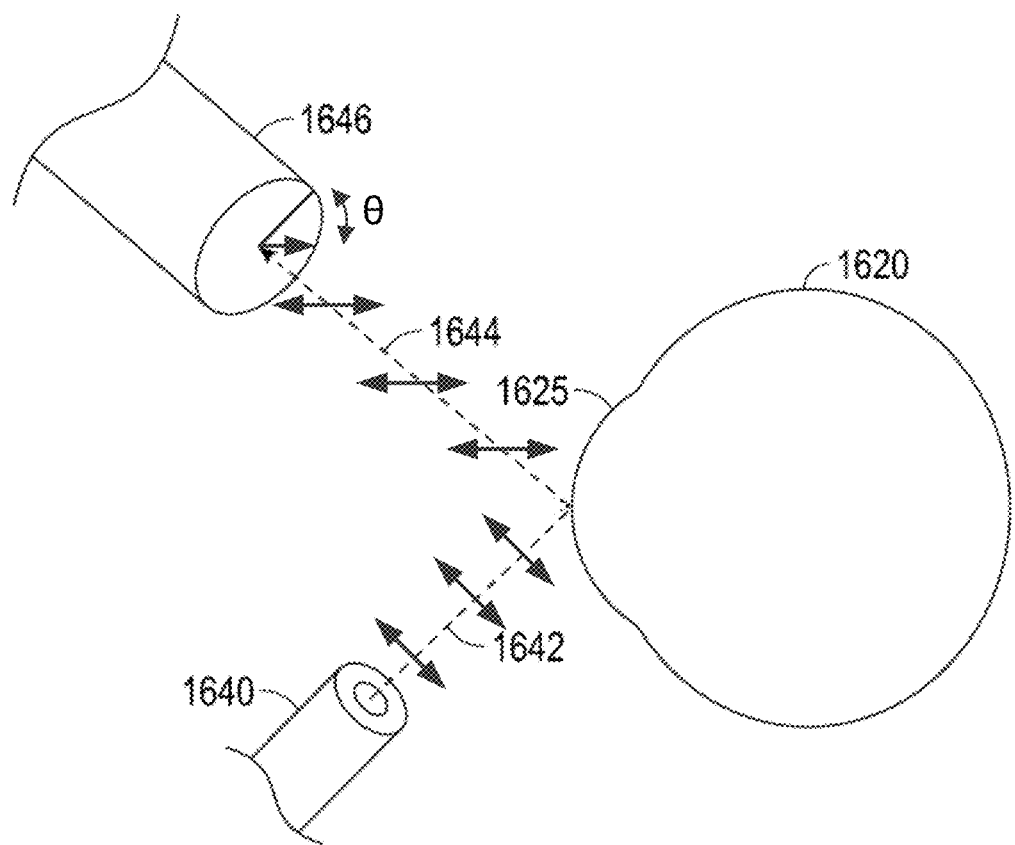

FIGS. 11A-11B schematically depict an example embodiment of an augmented reality/virtual reality wearable device 1600 that can be worn by a user configured to be used in a system or method for determining the user's glucose level. The device 1600 includes a frame 1664 attached to a display 1662. The display 1662 can be configured to be positioned forward of the eyes 1620 of the user. The device 1600 can be configured to project polarized light (e.g., linearly polarized light) 1642 from at least one light source 1640 into at least one eye 1620 of the user. A portion of the projected light can be reflected by the eye 1620 as light 1644 and the polarization angle of the reflected light 1644 can be rotated. The portion of the reflected light 1644 can be received by one or more light analyzers 1646 to determine the polarization angle rotation such that the level of glucose can be determined.

In various embodiments of the wearable device 1600 shown in FIGS. 11A-11B, the frame 1664 can have characteristics similar to the frame 64 of FIG. 2. In various embodiments of the wearable device 1600, the display 1662 can have characteristics similar to the display 62 of FIG. 2. The display 1662 can comprise a display lens attached to the frame 1664. For example, in some embodiments, the display 1662 can comprise a display lens mounted in the frame 1664. In some embodiments, the display 1662 can include a unitary lens comprising two ocular zones, each ocular zone positioned in front of the user's eyes 1620. In some embodiments, the display 1662 can comprise two display lenses attached to the frame 1664, each display lens comprising an ocular zone that is positioned in the front of each of the user's eyes 1620. As described herein, the display 1662 may include one or more transparent waveguides. As also described herein, the display 1662 of various embodiments can be configured to direct images to the user's eyes 1620. In some embodiments, a processor (e.g., processing electronics not shown) may be in communication with the display 1662 to control presentation of image content to the display 1662.

In certain embodiments, the device 1600 can include at least one light source 1640 configured to provide the polarized light to at least one eye 1620 of the user (e.g., towards the cornea 1625 shown in FIG. 11B). In various examples, one light source can be configured to provide polarized light to the left or right eye. In some examples, one light source can be configured to provide polarized light to the left eye and another light source can be configured to provide polarized light to the right eye. In some examples, more than one light source can be configured to provide polarized light to the left eye and/or more than one light source can be configured to provide polarized light to the right eye. In some examples, one or more light source can be configured to provide polarized light to both the left and right eyes (for example, using a beamsplitter).

As shown in FIG. 11A, one or more light sources 1640 can be positioned on the frame 1664. In other embodiments, one or more light sources 1640 can be positioned on the display 1662. In yet other embodiments, one or more light sources 1640 can be incorporated into and/or used with the light sources 2040 (in FIG. 6) used to provide illumination and/or images to the display (e.g., the light sources used to provide light into the waveguides).

The light source 1640 can be configured and/or positioned in the user-wearable device 1600 such that the polarized light 1642 can be directed towards at least one eye 1620 of the user. For example, in some cases, the light source 1640 can be positioned adjacent the user's eye 1620 such that the polarized light 1642 can be directed directly towards the user's eye 1620. The polarized light 1642 used in some embodiments may be a collimated beam of light directed towards the user's iris or retina (e.g., vasculature in the retina). In some cases, the polarized light 1642 can be directed towards the user's eye 1620 via redirections elements (e.g., lenses, prisms, mirrors, etc.).

Figure 11C:
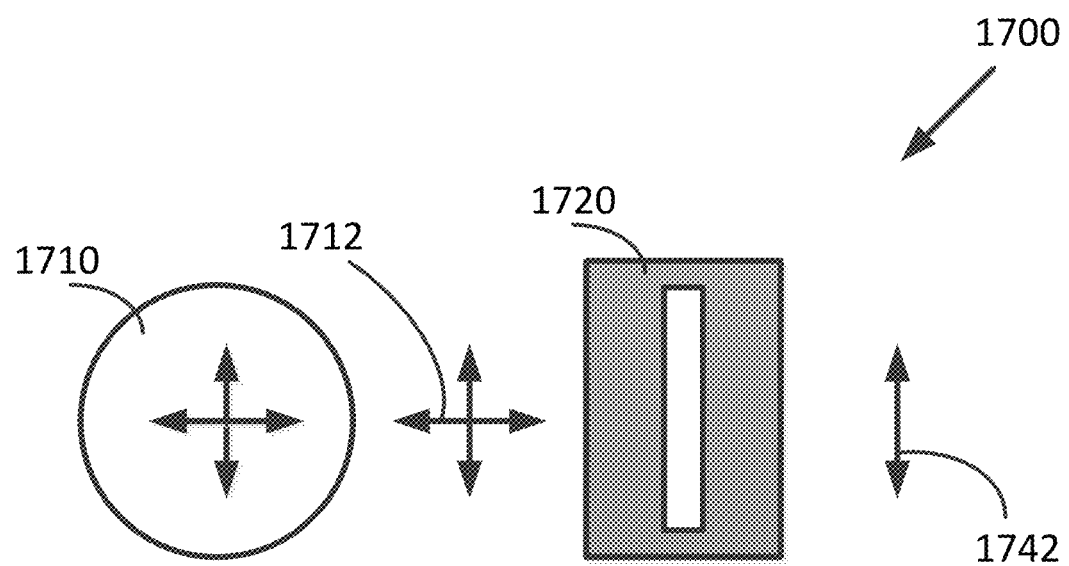
FIG. 11C schematically illustrates an example source of polarized light.

Any source of polarized light can be used, including any source of linearly polarized light, any source of circularly polarized light converted to linearly polarized light, any source of unpolarized light used with a polarizer, etc. FIG. 11C schematically illustrates one example source 1700 of polarized light. The light source 1700 can include a polarizing filter 1720 positioned in front of a source 1710 of unpolarized light 1712 to produce polarized light 1742. For example, the polarizing filter 1720 can include a filter with a preferential plane of transmission to linearly polarize the light. Thus, one or more light sources 1640 used in the device 1600 shown in FIGS. 11A-11B can polarize light through transmission (e.g., without being limited by theory, the light can be polarized consistent with the preferential plane of transmission as the unpolarized light is transmitted through the polarizing filter). In various embodiments of the user-wearable device 1600 shown in FIGS. 11A-11B, the polarized light source 1640 can include a polarizer utilizing one or more principles of light transmission, reflection, scattering, constructive interference, and/or destructive interference.

Figure 11D:
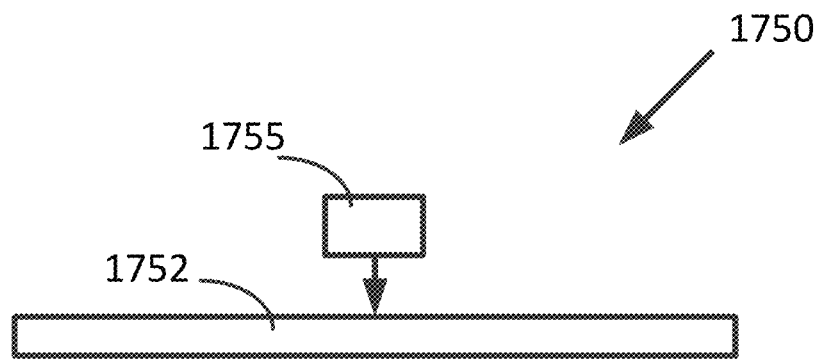
FIG. 11D schematically illustrates an example polarization controller.

FIG. 11D schematically illustrates an example polarization controller 1750 that can be used in another example source of polarized light. The polarization controller 1750 can include at least one optical fiber 1752. For example, the polarization controller 1750 can also include at least one actuator 1755 (e.g., metal plates and/or a piezo-electric actuator in some instances) configured to apply pressure on the optical fiber 1752. Without being limited by theory, the stress on the optical fiber 1752 can induce a phase shift between orthogonal polarization components. In various embodiments, the polarization controller 1750 can be configured to apply a pressure on the optical fiber 1752 such that the optical fiber 1752 can control the polarization state including polarization angle of polarized light output therefrom. In some embodiments, the light source 1700 can include a polarizing filter and a polarization controller.

Other examples of light sources and/or polarizers are possible. With reference back to FIGS. 11A-11B, the wavelength of the light source 1640 can be any wavelength and/or energy level, preferably not harmful to the human eye. For example, in some examples, the light source 1640 can include a source of light having a wavelength in the range from 400 nm to 800 nm, e.g., 450 nm to 800 nm, 470 nm to 800 nm, 480 nm to 800 nm, 490 nm to 800 nm, 500 nm to 800 nm, 500 nm to 750 nm, 500 nm to 700 nm, 500 nm to 650 nm, 500 nm to 600 nm, 500 nm to 550 nm, 550 nm to 570 nm, 550 nm to 580 nm, 550 nm to 590 nm, 550 nm to 600 nm, or any ranges formed by any values within these ranges. Without being bound by theory, wavelengths closer to 500 nm can yield more glucose rotation than higher wavelengths such as 700 nm in some instances. In some embodiments, a source of light having a wavelength in the range from 530 nm to 600 nm, 540 nm to 600 nm, 550 nm to 600 nm, 550 nm to 590 nm, or any range formed by any values within these ranges can be used to reduce potential harm to retinal cells due to smaller wavelengths.

In some embodiments, the light source 1640 can include a laser diode. In some embodiments, the light source 1640 can include a laser, such as a red helium-neon laser or an argon laser, having a power in the range from 1 mW to 20 mW, e.g., 1 mW to 15 mW, 1 mW to 12 mW, 2 mW to 15 mW, 3 mW to 15 mW, 5 mW to 10 mW, or any ranges formed by any of these values. Other example light sources are possible.

With continued reference to FIGS. 11A-11B, a portion of the projected polarized light 1642 can be reflected, scattered and/or diffracted by various anatomical features of the eyes 1620 of the user. The polarization angle of the projected light 1642 can be rotated by glucose molecules in the aqueous humor of the user's eye 1620 (e.g., as light transmits through the glucose molecules). The device 1600 can be configured to determine the polarization angle rotation of the reflected light 1644. For example, the device 1600 can include at least one light analyzer 1646 configured to determine the polarization angle rotation of the reflected light 1644. As described herein, the user's glucose level can be related to the amount of rotation. For example, in some examples, the amount of polarization angle rotation can be proportional (e.g., directly proportional in some instances) to the glucose concentration. Accordingly, various embodiments described herein include one or more light analyzers 1646 configured to determine the polarization angle rotation such that the user's glucose level can be determined.

One or more light analyzers 1646 can be positioned on the frame 1664. In other embodiments, one or more light analyzers 1646 can be positioned on the display 1662. The number of light analyzers 1646 is not particularly limited. In some examples, the number of light analyzers 1646 can correspond to the number of reflected light beams 1644. In some examples, one light analyzer 1646 can be used to determine the polarization angle rotation of more than one reflected light beam 1644.

As shown in FIG. 11B, at least a portion of the reflected light 1644 can be directed toward a light analyzer 1646. In some examples, the light analyzer 1646 can be positioned adjacent the user's eye 1620 such that the reflected light 1644 can be directed directly towards the light analyzer 1646. For example, a light analyzer 1646 can be positioned to receive reflected light 1644 based at least in part on the polarized light's angle of incidence on the user's eye 1620. In some cases, the reflected light 1644 can be directed towards the light analyzer 1646 via redirections elements (e.g., lenses, prisms, mirrors, etc.).

Figure 11E:
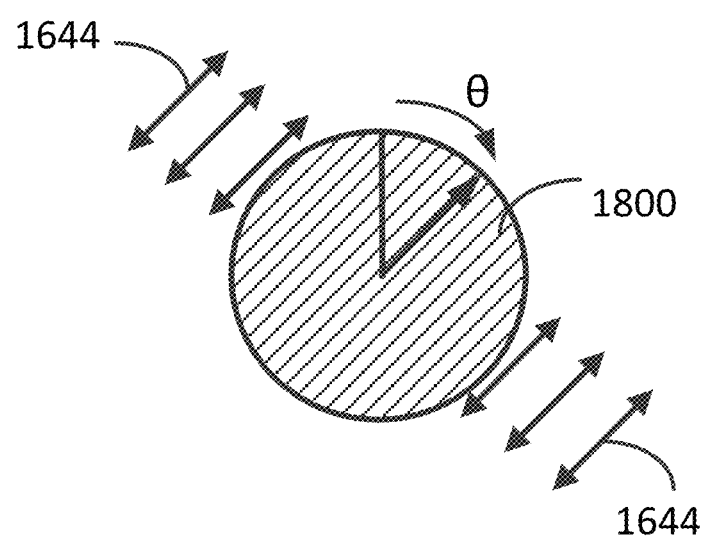
FIG. 11E schematically illustrates an example light analyzer comprising a filter.

With reference now to FIG. 11E, the light analyzer 1646 can include a polarizer such as polarizing filter 1800 similar to the polarizing filter 1720 shown in FIG. 11C, e.g., a polarizing filter with a preferential plane of transmission. The polarizing filter 1800 can be positioned such that the preferential plane of transmission is aligned with the original plane of transmission to indicate 0 degrees. If the reflected light 1644 had rotated, at least a portion of the light will be blocked by the polarizing filter 1800 because the polarization of the light is not aligned with the plane of transmission of the filter. In some embodiments, the polarizing filter 1800 can be configured to rotate such that the plane of transmission of the filter is aligned with the polarization of the reflected light 1644 and transmission will be increase or maximized. The polarization angle rotation of the reflected polarized light 1644 can be determined by the amount of rotation that causes the most reflected light 1644 to transmit through the polarizing filter 1800. In some embodiments, the polarizing filter 1800 can be configured to rotate such that the polarization angle rotation of the reflected polarized light 1644 can be determined when the reflected light 1644 is blocked by the polarizing filter 1800. The polarization filter is rotated until the plane of polarization of the polarization filter is "crossed" with respect to the polarization of the reflected light and the polarization filter does not allow the polarized light to pass therethrough. The angle of rotation of the polarization caused by the glucose can be determined based on the amount the polarization filter was rotated. The light analyzer 1646 can include processing electronics configured to determine the angle of rotation. In some embodiments, the processing electronics configured to determine the polarization angle rotation may be incorporated into the processing electronics configured to control presentation content to the display 1662. The polarization angle rotation determined by the light analyzer 1646 can be used to determine the user's glucose level.

Other types of light analyzers 1646 and/or polarizers can be used. For example, the light analyzer 1646 may include a stationery polarizing filter 1800. In some such embodiments, the linearly polarized light 1644 may be rotated by rotating the light source 1640 (e.g., rotating the polarizing filter 1720 shown in FIG. 11C). The light analyzer 1646 including a stationary polarizing filter 1800 can be used to determine the polarization angle rotation of the rotating polarized light, for example, in a manner similar to that described above.

In some embodiments, the glucose level can be determined by a processor such as processing electronics either incorporated into the user-wearable device 1600 or as a separate component connectable to the user-wearable device 1600. The processing electronics can be incorporated locally in the device 1600. In some examples, the processing electronics can be integrated with the electronics configured to control image content to the display 1662. As another example, the processing electronics can be integrated with the electronics of the light analyzer 1646 that determines the polarization angle rotation. In some such examples, the light analyzer 1646 not only determines the polarization angle rotation, but can also be configured to determine the user's glucose level based at least in part on the polarization angle rotation. In some embodiments, the light analyzer 1646 may also include memory to access and/or store data, such as in a database of the determined polarization angle rotations, the determined glucose levels, and/or information relating to the determined glucose levels.

Figure 12:
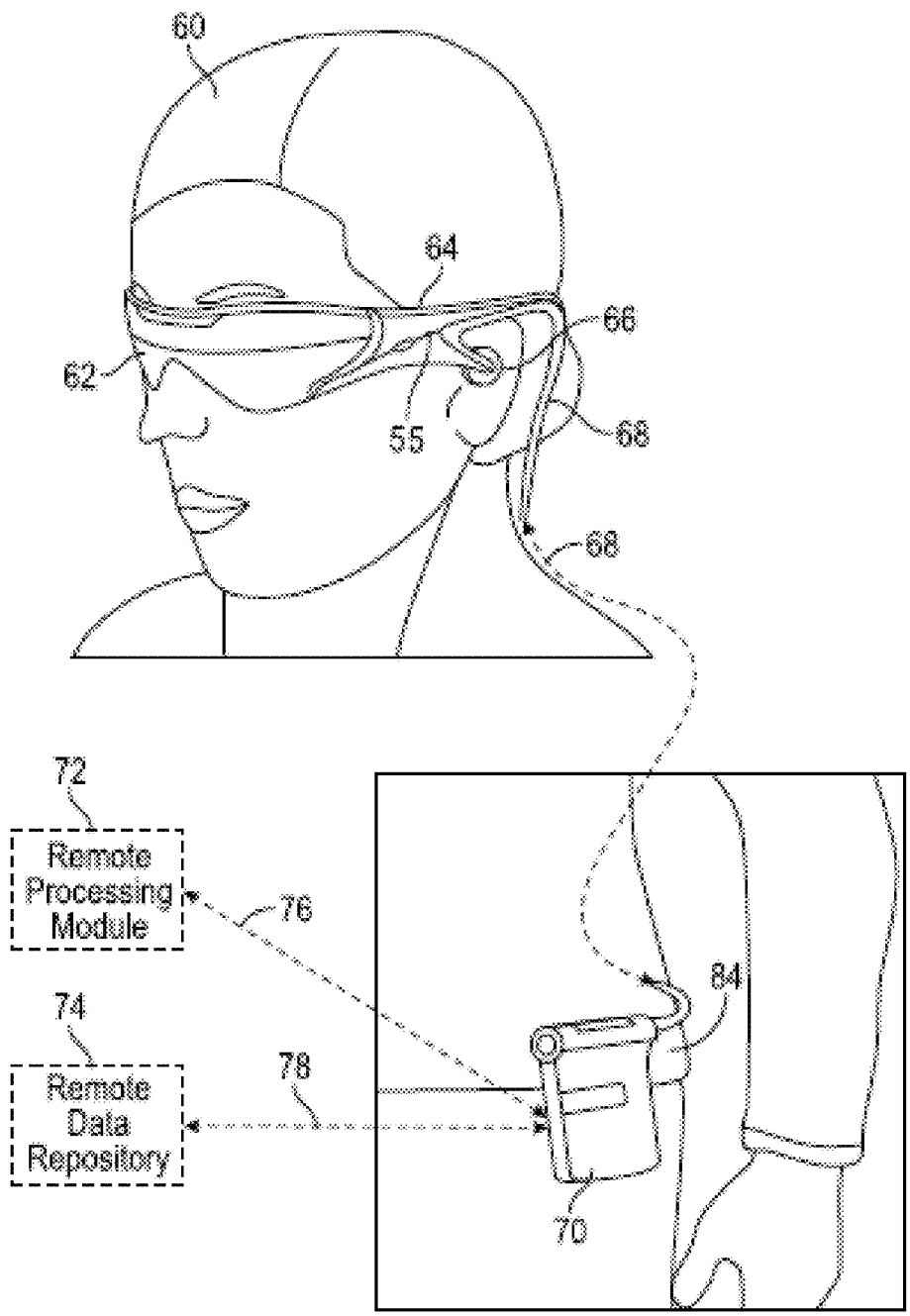
FIG. 12 schematically illustrates an example augmented reality display system in a belt-coupling style configuration.

As another example, the processing electronics can be included in the local processing and data module 70 as shown in FIGS. 2 and 10. The local processing and data module 70 can be operatively coupled (e.g., by a wired lead or wireless connectivity) to the user-wearable device 1600. The local processing and data module 70 can be mounted in a variety of configurations as described herein, including being removably attached to the torso 84 of the user 60 in a belt-coupling style configuration as shown in the example embodiment of FIG. 12. Some belt-coupling style configurations can also advantageously provide a battery and/or light source 1640 attached to the belt. Other configurations are possible. In various embodiments, the local processing and data module 70 can determine the level of glucose based at least in part on the amount of polarization angle rotation, e.g., determined by the light analyzer 1646. In various embodiments, the local processing module 70 can access and/or store data, such as in a database of the determined rotations, the determined glucose levels, and/or information relating to the determined glucose levels.

Additionally and/or alternatively, the processing electronics can be included in a remote processing module. For example, the processing electronics can be incorporated in the remote processing module 72 and/or remote data repository 74 shown in FIGS. 2 and 12. In some examples, the remote processing module 72 and/or remote data repository 74 can be operatively coupled to the local processing and data module 70, e.g., by communication links 76, 78, such as via a wired or wireless communication links, such that these remote modules 72, 74 can be operatively coupled to each other and available as resources to the local processing and data module 70. In various such embodiments, the remote processing module 72 can be configured to determine the level of glucose based at least in part on the polarization angle rotation, e.g., determined by the light analyzer 1646. In some embodiments, the remote processing module 72 can access and/or store data in the remote data repository 74, such as in a database of the determined rotations, the determined glucose levels, and/or information relating to the determined glucose levels.

The glucose concentration can be proportional (e.g., directly proportional in some instances) to the amount of polarization angle rotation. Thus, in various embodiments, the processing electronics (e.g., the processing electronics incorporated in the processing electronics controlling presentation content to the display 1662, associated with the light analyzer 1646, in the local processing and data module 70, and/or in the remote processing module/remote data repository 72, 74) can determine the user's glucose level based at least in part on the determined polarization angle rotations. In various embodiments, the glucose level can be expressed as a quantitative value, e.g., a glucose concentration. In some examples, the processing electronics may determine the glucose level based on a calculation (e.g., calculating with an equation relating the polarization angle rotation to the glucose level). Additionally and/or alternatively, the processing electronics may determine the glucose level based on information in a database (e.g., consulting a database correlating the determined polarization angle rotation with glucose levels). In some embodiments, the glucose level can be expressed on a qualitative scale, e.g., "normal," "abnormal," "high abnormality," etc.

The user-wearable device 1600 can be configured to communicate with the user and/or with a clinician. In some embodiments, the user may input a command and/or information to the user-wearable device 1600. The user-wearable device 1600 may, for example, be configured to perform the above described glucose testing upon request by the user. As an example, the user-wearable device 1600 may initiate glucose testing when the user activates (e.g., turns on) the polarized light source 1640. As another example, the user-wearable device 1600 may initiate glucose testing and activate the polarized light source 1640 when the user commands the user-wearable device 1600 to perform glucose testing.

The user-wearable device 1600 may include a user interface to allow the user to input the command and/or information. In some embodiments, the user-wearable device 1600 may include a physical user interface. As an example, one or more buttons or switches may be provided on the surface of the user-wearable device 1600 such as on a surface of the frame 1664. In some embodiments, the user-wearable device 1600 may include a virtual user interface. As an example, one or more icons on a virtual touch screen may be provided on the display 1662 and/or on a display separate from display 1662 (e.g., on a display on a component that houses the local processing module 70 in FIG. 12). The device may therefor include outwardly, e.g., forwardly facing cameras, that are configured to provide gesture recognition to receive input from the user via gestures. For example, processing electronics may receive image based signals produced by the outwardly facing camera to detect and/or identify gesture or other movements of the user. In some embodiments, the user-wearable device 1600 may include an audio recognition system such that the user can input commands and/or information by voice. As yet another example, the user-wearable device 1600 may include a movement recognition system (e.g., a motion detector) to recognize when the user is wearing the device 1600 and to initiate glucose testing.

In some examples, the user-wearable device 1600 may be configured to communicate with the user via a display to request information from the user and/or to display results. For example, the user-wearable device 1600 can be configured to communicate the determined polarization angle rotation and/or the determined glucose level or other message to the user and/or clinician on display 1662. The message, for example, can be a suggestion to visit a physician or other health care provider or to take medication. As another example, the user-wearable device 1600 can be configured to communicate such example information on a display separate from display 1662, e.g., on a display on a component that houses the local processing module 70 in FIG. 12.

Although the user-wearable device 1600 may be configured to perform glucose testing upon user request, the device 1600 may also be configured to perform glucose testing automatically for a certain period of time, eliminating the need for a user to set timers and disrupt his or her day. For example, the user-wearable device 1600 may be configured to perform glucose testing automatically as programmed into the device 1600 without user request. As another example, after the user requests glucose testing to be performed, the user-wearable device 1600 may automatically perform glucose testing until the user requests the testing to be paused. The device 1600 may automatically perform glucose testing for a certain frequency within a certain period of time (e.g., as requested by the user or clinician). In some embodiments, the user-wearable device 1600 may perform glucose testing at least 1, 2, 3, 4, 5, 6, 7, 8, 9, 10, 12, 15, 17, or 20 times a day or more. In some embodiments, the user-wearable device 1600 may perform glucose testing at least 1, 2, 3, 4, 5, 6, 7, 8, 9, 10, 12, 15, 17, or 20 times a week or more. In some embodiments, the user-wearable device 1600 may perform glucose testing at least 1, 2, 3, 4, 5, 6, 7, 8, 9, 10, 12, 15, 17, or 20 times a month or more. In some embodiments, the user-wearable device 1600 may perform glucose testing at least 1, 2, 3, 4, 5, 6, 7, 8, 9, 10, 12, 15, 17, or 20 times a year or more. Any ranges between the values above are also possible.

In some examples including (or operatively coupling to) processing electronics that are configured to access and/or store data (e.g., in the light analyzer 1646, in local data module 70 and/or in a remote data repository 74), the user-wearable device 1600 can be configured to track the user's glucose level over time. In some such examples, the user-wearable device 1600 (e.g., via the processing electronics) can be configured to compare the contemporaneous glucose level with historical glucose levels. The user-wearable device 1600 may include alarm systems to provide audible, visual, graphic and/or tactile alerts to the user and/or to a clinician when an abnormally high glucose level or other anomaly is determined. In some embodiments, the tracked data can be remotely shared with the user's doctor.

Test results for any test can be patient specific. For glucose testing, equations used to determine glucose levels may vary for different patient populations (e.g., different ages, sizes, ethnicity, etc.). Various embodiments described herein may individualize the test results by calibrating the determined glucose levels based on information regarding the user. For example, in some embodiments, the user-wearable device 1600 may calibrate the determined glucose levels based on the glucose level determined by blood testing. In some such embodiments, the user-wearable device 1600 may request on occasion that the user take a blood test. The user or clinician can input the results of such a test to allow the user-wearable device 1600 to calibrate its determined glucose levels. Since a relatively large amount of data can be gathered, in many instances after the device 1600 is initially calibrated (or after a few calibrations), the device may be configured such that the user may no longer need to perform glucose blood testing.

Glucose levels may also be affected by various factors. For example, normal glucose levels may be in the range of 70-99 mg/dL when the user is fasting (e.g., no food for 8 hours). However, glucose levels may be higher when the user is not fasting. Normal levels may be considered in the range of 70-140 mg/dL two hours after eating. Accordingly, some embodiments may occasionally request information (e.g., whether fasting, time of last meal, whether taking medication, time of last medication, etc.) from the user and may consider such responses when evaluating the determined glucose levels (e.g., when comparing contemporaneous glucose level with historical glucose levels).

By gathering additional information from the user, various embodiments can provide even more accurate and individualized results and assessments. Additional information regarding the user (e.g., parameters relating to a physical state of the user, the user's activities, environmental conditions, etc.) can also be acquired by the use of one or more sensors. With reference to FIG. 10, some embodiments can include one or more user sensors (e.g., an inwardly facing camera in some examples) 24, 30, 32 and/or one or more environmental sensors (e.g., an outwardly facing camera in some examples) 28, 34. As one example, an inwardly facing camera 24 and/or an outwardly facing camera 28 may be provided to capture the user's activities (e.g., eating, exercising, etc.). As another example, a microphone 67 (FIG. 2) may capture sounds indicative of chewing by the user. The chewing sound can also be indicative of certain foods. Certain embodiments can determine whether the user is fasting when performing glucose testing based on the time elapsed since the user's last meal. As described herein, glucose levels can increase when the user has not been fasting and such information may be considered when reviewing the determined glucose levels. In addition, various embodiments can be configured to determine relationships between the determined glucose level and at least one aspect of the user or the user's environment. For example, some embodiments can be configured to correlate changes in a user's glucose level with information relating to the user or the user's environment.

Some embodiments can automatically record a food intake diary (e.g., a log of food consumed and/or the nutritional information of the food consumed). For example, an outwardly facing camera can capture the user's food intake and eating habits. The user-wearable device 1600 (e.g., via processing electronics) can identify certain foods (including beverages) and obtain the breakdown of the nutritional information (e.g., sugars, carbohydrates, protein, fat, cholesterol, sodium, etc.) from a database (e.g., stored locally or remotely). In some instances, the food may be recognizable in the database (e.g., a frozen dinner). However, in other instances, the food may not be recognizable (e.g., a home cooked meal). In some such instances, the user-wearable device 1600 may request the user for input. The input can be saved in the database for future reference. In various embodiments, the nutritional breakdown can be presented automatically (or upon user request) to the user in real time via the display 1662 or a display separate from display 1662. The user can decide whether or not to continue eating and/or to control the intake portion. Certain embodiments can also analyze the food intake diary to find trends. For example, if historically when the user eats a certain food (e.g., a bowl of cereal or a cheeseburger) and his or her glucose level increases, the device and/or system 1600 can provide an alert to the user. By monitoring food intake and/or nutritional information of food consumed, various embodiments can help a user maintain a glucose level within a targeted range.

As described herein, various embodiments can be programmed to perform a glucose test at a certain time and/or frequency. Some embodiments can also automatically perform a glucose test when certain activities are performed or after a specified time from the activity. For example, the device and/or system 1600 may be programmed to perform a glucose test when the user is eating, two hours after eating, etc.

As another example, temperatures can affect glucose levels. For example, dehydration on a hot day can cause glucose in the blood to become more concentrated. On the other hand, dilation of blood vessels on a hot day can cause glucose levels to decrease. Further, the body can use more energy in trying to stay cool (or to stay warm in cold temperatures). Some embodiments of the user-wearable device 1600 can include a sensor to sense the temperature (e.g., an environmental temperature sensor). Based at least in part on the sensed environmental temperature, the user-wearable device 1600 can determine the glucose level for the given temperature. If the temperature is outside of the calibrated range (e.g., outside the temperature range), the device 1600 can be configured to provide an alert to the user, for example, to take another reading later.

In some instances, the user's temperature may be different than the environmental temperature. For example, although the weather may be freezing, the user may be wearing a sweater, scarf, hat, and heavy coat. Some embodiments of the user-wearable device 1600 can include a sensor to sense the user's temperature (e.g., a user temperature sensor on the user's forehead). Based at least in part on the sensed body and/or skin temperature, the user-wearable device 1600 can determine the glucose level for the given temperature. If the user's temperature is outside of the calibrated range (e.g., outside the temperature range), the device 1600 can be configured to provide an alert to the user, for example, to take another reading later.

As yet another example, physical exertions can also affect glucose levels. For example, glucose can be lost through perspiration. Some embodiments can include a sensor (e.g., an inwardly facing camera) to determine whether the user is sweating and/or a sensor (e.g., an outwardly facing camera) to determine whether the user is exercising. If the user is sweating and/or exercising, such information can be considered when evaluating the results. In some instances, the user-wearable device 1600 may also monitor the user's heart rate and/or respiration rate and correlate the determined glucose level with such information. Some embodiments can also automatically perform a glucose test when certain conditions are detected (e.g., certain conditions can trigger the device 1600 to perform a glucose test). For example, the device 1600 may be programmed to perform a glucose test when the device 1600 senses the user is behaving abnormally, e.g., sweating, walking at a slower pace than usual, etc.

Thus, in various embodiments, the user-wearable device 1600 can be configured to detect at least one parameter relating to a physical state of the user (e.g., temperature, heart rate, respiration rate, amount of sweating, time elapsed after fasting, etc.), and analyze the determined glucose level based at least in part on the parameter. The device 1600 can also provide an alert to the user or clinician when the parameter falls outside a range. In addition, certain embodiments can be configured to detect an activity or condition of the user (e.g., eating). The device 1600 can also provide real time feedback relating to the activity or condition to the user. For example, the device 1600 can provide alerts that the food the user is eating has historically resulted in higher glucose readings. As another example, based on the determined glucose level (e.g., a relatively high glucose reading), the device 1600 can also advise the user to retake a glucose test (e.g., by a blood test and/or using the device). In some instances, the device 1600 can be configured to automatically re-determine the glucose level.

In addition, one or more of the sensors may include one or more eye tracking sensors (e.g., an inwardly facing camera). Some such sensors can be configured to determine if the provided polarized light 1642 did not transmit to the eye 1620. The user-wearable device 1600 may be configured not to determine the glucose level when the eye tracking sensor determines that the polarized light did not transmit to the user's eye or possibly a target area of the eye such as the iris, retinal vasculature, or the same area of the eye (for example, to maintain calibration).

Figure 13:
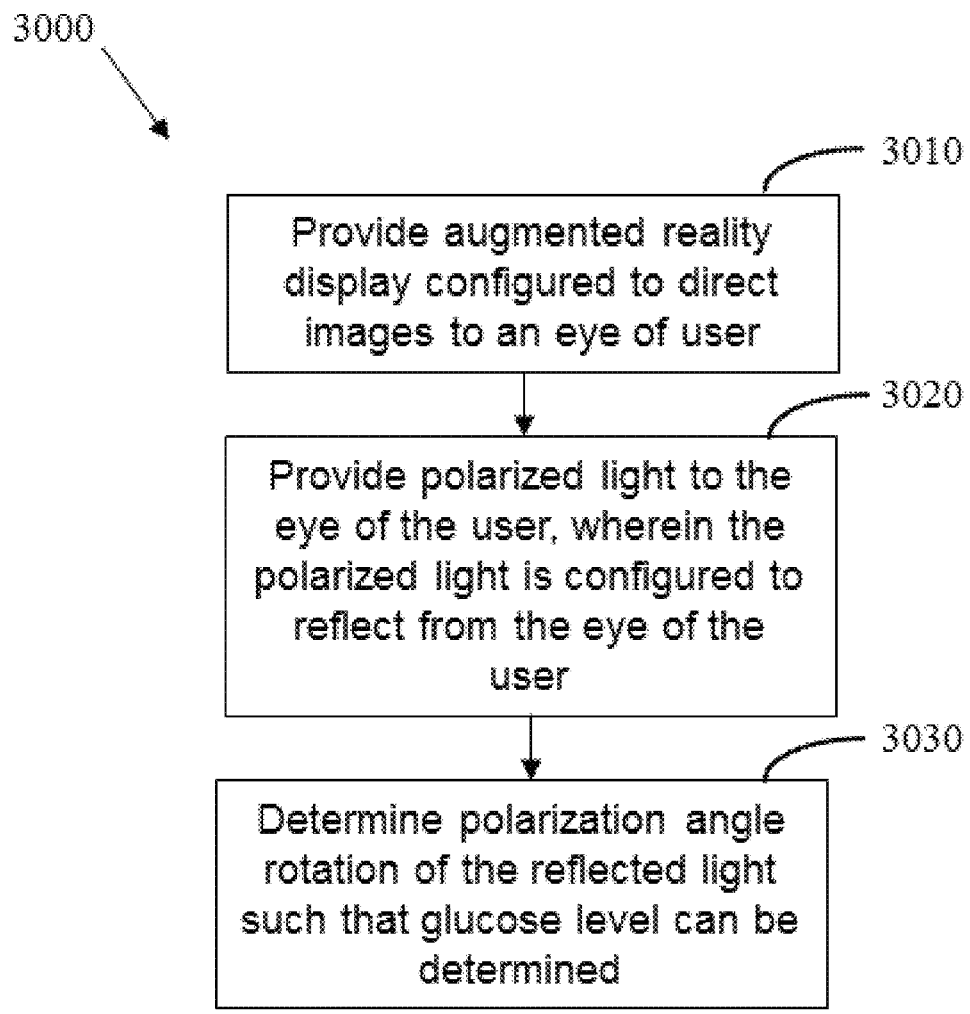
FIG. 13 is an example process flow for determining glucose level.

With reference now to FIG. 13, an example method 3000 of determining glucose levels is illustrated. The method 3000 can include providing an augmented reality display configured to direct images to an eye of the user as shown in block 3010. The augmented reality display may include the example display devices 80, 1000, 2010, or 1600 in FIG. 2, 6, 10, or 11A respectively. The display device may include, for example, a head-mounted display device that projects image content to the user's eyes.

In some embodiments, a head-mounted display device can be configured to present to the user augmented reality image content using a display. In certain embodiments, the display can be disposed on the frame of the head-mounted display. As described herein, the display can include one or more transparent waveguides disposed at a location in front of the user's eyes. Accordingly, a user may be able to see through the display. Light from objects in the environment in front of the user wearing the head mounted display device can be transmitted through the display, e.g., through the one or more transparent waveguides into the user's eye such that images of the environment in front of the user or at least a portion thereof is formed on the retina of the user's eye.

At block 3020, the user-wearable device may be configured to provide polarized light to the eye of the user such that the polarized light is configured to reflect from the eye of the user. In some embodiments, the polarized light can be provided by a polarizing filter. In some embodiments, the polarized light can be provided by a polarization controller, e.g., an actuator configured to provide pressure on an optical fiber. The actuator can include a piezo-electric actuator in some instances.

At block 3030, various embodiments may determine polarization angle rotation of the reflected light such that the glucose level can be determined. In various embodiments, the glucose level can be determined based at least in part on a calculation relating the polarization angle rotation with the glucose level (e.g., glucose concentration). In some embodiments, the glucose level can be determined based at least in part on a database correlating polarization angle rotation with glucose levels.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module 70, the remote processing module 72, and remote data repository 74. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Accordingly, the claims are not intended to be limited to the embodiments shown herein, but are to be accorded the widest scope consistent with this disclosure, the principles and the novel features disclosed herein. For example, although many examples within this disclosure are provided with respect to medical applications in the medical field, certain embodiments described herein may be implemented for a wide variety of other applications and/or in numerous other contexts.

What is claimed is:

1. A user-wearable device comprising:
a frame configured to mount on a user;
a display attached to the frame, the display configured to direct virtual images to an eye of the user and to transmit light from a surrounding environment to the eye of the user to allow a view of that surrounding environment;
a light source configured to provide polarized light to the eye of the user, wherein the polarized light is configured to reflect from the eye of the user;
one or more sensors configured to determine if the provided polarized light transmits to the iris of the user; and
a light analyzer configured to determine a polarization angle rotation of the reflected light from the eye of the user such that a glucose level of the user can be determined based at least in part on the polarization angle rotation of the reflected light,
wherein the light source comprises a polarization controller comprising at least one optical fiber and at least one piezo-electric actuator configured to apply pressure on the at least one optical fiber such that the optical fiber controls a polarization state of the polarized light provided to the eye of the user.

2. The user-wearable device of claim 1, wherein the light source comprises a polarizing filter.

3. The user-wearable device of claim 1, wherein the light source comprises a source of light having a wavelength in the range of 500 nm to 800 nm.

4. The user-wearable device of claim 1,
wherein the light analyzer comprises a rotatable filter.

5. The user-wearable device of claim 1, further comprising processing electronics configured to determine the glucose level of the user based at least in part on the polarization angle rotation of the reflected light.

6. The user-wearable device of claim 5, wherein the processing electronics is configured to determine a concentration of the glucose level based at least in part on the determined polarization angle rotation of the reflected light.

7. The user-wearable device of claim 5, wherein the processing electronics is configured to determine the glucose level automatically for at least a period of time.

8. The user-wearable device of claim 7, wherein the processing electronics is configured to:
determine whether to re-determine the glucose level; and
if determined, automatically re-determine the glucose level.

9. The user-wearable device of claim 5, wherein the processing electronics is configured to remotely store and access the determined glucose level and/or information relating to the determined glucose level.

10. The user-wearable device of claim 9, wherein the device is configured to track the glucose level of the user over time.

11. The user-wearable device of claim 10, wherein the device is configured to compare a contemporaneous glucose level with a historical glucose level.

12. The user-wearable device of claim 11, wherein the device is configured to provide an alert to the user or clinician in response to comparing the contemporaneous glucose level with the historical glucose level.

13. The user-wearable device of claim 1, further comprising one or more sensors configured to detect at least one parameter relating to a physical state of the user.

14. The user-wearable device of claim 13, wherein the at least one parameter comprises body temperature, skin temperature, heart rate, respiration rate, level of sweating, time elapsed since last meal, or time elapsed since last medication.

15. The user-wearable device of claim 13, wherein the device is configured to analyze the determined glucose level based at least in part on the at least one parameter relating to the physical state of the user.

16. The user-wearable device of claim 13, wherein the device is configured to provide an alert to the user or clinician when the at least one parameter falls outside a range.

17. The user-wearable device of claim 1, further comprising an optical detector disposed with respect to the analyzer to detect the amount of polarized light reflected from the eye that passes through the analyzer.

18. The user-wearable device of claim 1, further comprising one or more sensors configured to detect an activity or condition of the user.

19. The user-wearable device of claim 18, wherein the activity comprises eating, taking medication, exercising, or a combination thereof.

20. The user-wearable device of claim 18, wherein the device is configured to provide real time feedback relating to the activity or condition to the user.

21. The user-wearable device of claim 1, wherein the device is configured to not determine the glucose level when the one or more sensors determine the polarized light did not transmit to the iris of the user.

22. The user-wearable device of claim 1, wherein the one or more sensors comprise one or more eye-tracking sensors.

23. The user-wearable device of claim 1, wherein the one or more sensors comprise one or more cameras.

24. The user-wearable device of claim 1, wherein the at least one piezo-electric actuator is configured to apply pressure on the at least one optical fiber such that the optical fiber rotates the polarization state of the polarized light provided to the eye of the user.

* * * * *